United States Patent [19]

Mallams et al.

[11] Patent Number: 4,808,575

[45] Date of Patent: Feb. 28, 1989

[54] 12,13-OXODERIVATIVES OF MACROLIDES

[75] Inventors: Alan K. Mallams, West Orange; Randall R. Rossman, Nutley, both of N.J.

[73] Assignee: Schering Corporation, Kenilworth, N.J.

[21] Appl. No.: 877,079

[22] Filed: Jun. 23, 1986

[51] Int. Cl.[4] .................. A61K 31/70; C07H 17/08
[52] U.S. Cl. ................................. 514/30; 536/7.1
[58] Field of Search ........................ 519/30; 536/7.1

[56] References Cited

U.S. PATENT DOCUMENTS

| | | | |
|---|---|---|---|
| 4,321,361 | 3/1982 | Baltz et al. | 536/7.1 |
| 4,357,325 | 11/1982 | Ose et al. | 536/7.1 |
| 4,559,301 | 12/1985 | Turner et al. | 536/7.1 |

*Primary Examiner*—Johnnie R. Brown
*Assistant Examiner*—Elli Peselev
*Attorney, Agent, or Firm*—Thomas D. Hoffman; Gerald S. Rosen

[57] ABSTRACT

12,13-Oxo derivatives of 16-membered macrolides such as tylosin and 23-O-demycinosyltylosin useful as antibacterials are disclosed.

15 Claims, No Drawings

12,13-OXODERIVATIVES OF MACROLIDES

BACKGROUND AND SUMMARY

This invention relates to 12,13-oxo derivatives of 16 membered macrolides, e.g., tylosin and 23-demycinosyltylosin, pharmaceutical compositions containing them and methods of treating susceptible bacterial infections using such pharmaceutical compositions.

Sixteen membered macrolide antibiotics containing dienone chromophores are well known in the art. Tylosin is a naturally occurring macrolide antibiotic disclosed in U.S. Pat. No. 3,178,341. Other related macrolides are disclosed in U.S. Pat. No. 4,341,770 (5-O-mycaminosyltylonolide) (OMT), U.S. Pat. No. 4,321,361 (demycinosyltylosin) (DMT), U.S. Pat. No. 4,321,362 (demycinosyloxytylosin) (DMOT), U.S. Pat. No. 4,334,019 (demycinosyloxytylosin) and U.S. Pat. No. 4,443,436 (C-20 derivatives of tylosin, desmycosin, macrocin and lactenocin).

Numerous other sixteen-membered macrolide antibiotics appear in the article entitled "Macrolides" in Kirk-Othmer, Encyclopedia of Chemical Technology, third edition, vol. 2 p. 937 et sec. (1978).

Naturally occuring 16 membered epoxyenone or oxoenone macrolide antibiotics are well known. Rosaramicin is a 16 membered 12,13-oxoenone macrolide isolated from fermentation of *Micromonospora rosaria* (see U.S. Pat. No. 4,161,523). Mycinamicin I and II are other naturally occuring macrolides disclosed in U.S. Pat. No. 4,307,085. Various 12,13-epoxy derivatives of mycaminosyltylonide derivatives are disclosed in U.S. Pat. No. 4,454,314. See also U.S. Pat. No. 4,477,443 wherein 12,13-oxomycaminosyltylonolide, and the 4'-deoxy and 23-deoxy-23-dimethylamino derivatives are disclosed.

H. Tanaba, et al. (Paper 1150, 23th ICAAC, Minneapolis, Minn., Sept. 29, 1985) disclosed isolation of a naturally occurring 12,13-oxo-23-demycinosyloxytylosin, identified as M-119-a.

It would be desirable to have 16-membered oxoenone macrolides which exhibit enhanced antibacterial activity and high serum levels compared to those of other macrolides such as for example erythromycin, rosaramicin, and tylosin.

SUMMARY OF THE INVENTION

This invention provides a compound having the formula I

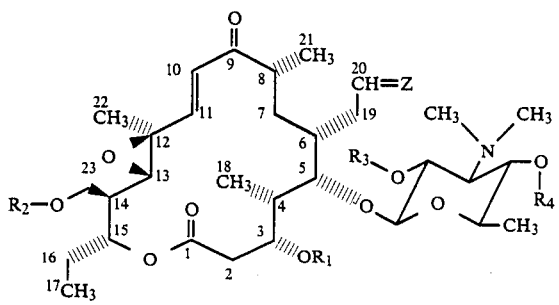

wherein
$R_1$ = H or an acyl group;
$R_2$ = H, an acyl group or

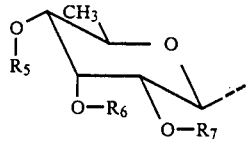

$R_3$ = H or an acyl group;
$R_4$ = H, an acyl group or

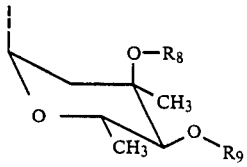

$R_5$ = H or an acyl group;
$R_6$ is H or methyl and
$R_7$ is methyl;
$R_8$ is H or an acyl group;
$R_9$ is H or an acyl group;
Z is oxygen, —NNH—aralkyl, —NNHCNH$_2$, —NNHCNH$_2$ or
          $\overset{\|}{O}$       $\overset{\|}{S}$ $$=N-N\begin{matrix}CH_2-(CH_2)_n\\ \\ CH_2-CH_2\end{matrix}Q$$

wherein
n is 0, 1 or 2 and Q $CR_{10}R_{11}$, $NR_{10}$, O, S, SO$_2$, $CR_{10}OR_{11}$,

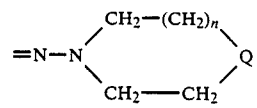

$$\overset{O}{\underset{\|}{CR_{10}-O-C-R_{11}}}, \overset{O}{\underset{\|}{CHCOR_{10}}} \text{ or } \overset{O}{\underset{\|}{CH-CNR_{10}R_{11}}},$$

wherein
$R_{10}$ and $R_{11}$ are independently hydrogen, lower alkyl, aralkyl, X-substituted aralkyl, aryl and X-substituted aryl wherein X is independently halogen, trifluoromethyl, lower alkoxy or (C$_2$-C$_7$) alkanoyl; with the proviso that when $R_4$ is H or an (C$_2$-C$_6$) alkanoyl, $R_2$ is other than H;
or a pharmaceutically acceptable acid addition salt thereof.

The compounds of this invention show high serum levels and are useful as antibacterials against susceptible bacterial infections, especially those caused by Gram-positive organisms.

This invention also provides pharmaceutical compositions comprising the compounds represented by formula I and to methods of treating susceptible bacterial infections, wherein an antibacterially effective amount of a compound or pharmaceutical composition thereof is administered to a mammal in need of such treatment.

It is to be understood that the stereochemical configuration of the structure of compounds of formula I is identical to that of tylosin.

DETAILED DESCRIPTION OF THE INVENTION

By the term "acyl group" as used herein is meant (C$_2$–C$_7$) alkanoyl; (C$_2$–C$_7$) alkanoyl substituted by chloro, lower alkoxy, aryl or aryloxy; aroyl; and aroyl or aryloxy substituted by one or more of halogen, nitro, lower alkoxy, or lower alkyl.

The term "lower alkyl" as used herein means straight and branched-chain alkyl groups of one to six carbons including methyl, ethyl, propyl, butyl, pentyl, hexyl and the corresponding branched-chain isomers thereof such as iso-propyl, tert or sec-butyl, iso-valeryl and iso-hexyl. Methyl is the preferred alkyl group.

The term "lower alkoxy" means alkoxy wherein the alkyl portion contains one to six carbons in a straight or branched chain groups including methoxy, ethoxy, propoxy, iso-butoxy, iso-valeroxy, pentoxy and sec-hexoxy.

The term "aryl" means phenyl and biphenyl.

The term "halogen" means fluoro, chloro and bromo, preferably fluoro and chloro.

The term "aralkyl" refers to lower alkyl substituted by aryl (phenyl and biphenyl) including benzyl, phenethyl and o-tolylethyl.

The term "(C$_2$–C$_7$) alkanoyl" means carbonyl groups univalently bonded to "lower alkyl" groups and includes unsubstituted and substituted acetyl, propionyl, butyryl, pentanoyl, hexanoyl, iso-butyryl and iso-valeryl. The preferred (C$_2$–C$_7$) alkanoyl groups are acetyl, butyryl, iso-valeryl for R$_1$, R$_2$, R$_3$, R$_4$, R$_5$, R$_8$ and R$_9$. For R$_2$ and R$_9$, iso-valeryl is more preferred.

Typical suitable chloro-substituted (C$_2$–C$_7$) alkanoyl groups include 2-substituted chloro(C$_2$–C$_7$) alkanoyl such as 2-chloroacetyl and 2-chloropropionyl. Typical suitable lower alkoxy(C$_2$–C$_7$)alkanoyl include methoxyacetyl, ethoxyacetyl methoxypropanoyl and propoxyacetyl. Typical suitable aryl-substituted (C$_2$–C$_7$)alkanoyl groups include phenylacetyl and biphenylacetyl. Typical suitable aryloxy-substituted (C$_2$–C$_7$) alkanoyl include phenoxyacetyl and biphenyloxyacetyl.

The term "aryloxy" means substituted and unsubstituted phenoxy and biphenyloxy.

Typical suitable substituted aryloxy groups include, p-chlorophenoxy, 3-chloro-4-nitrophenoxy, 4-propoxyphenoxy, 4'-methylbiphenoxy, 4-nitrophenoxy, 3-nitro-4-propylphenoxy.

The terms "aroyl" means substituted and unsubstituted benzoyl wherein the substituents are one or more of halogen, nitro, lower alkoxy or lower alkyl, e.g., 4-fluorobenzoyl, 3-chlorobenzoyl, 4-nitrobenzoyl, 3-nitrobenzoyl, 4-ethoxybenzoyl, 3-chloro-4-nitrobenzoyl, 3-fluoro-4-methoxybenzoyl, 3-nitro-4-ethylbenzoyl and 3-chloro-4-methylbenzoyl.

Exemplary compounds of the formula I include (a) compounds wherein Z=oxygen, i.e., 12,13-oxodesmycosin, 12,13-oxotylosin and 23-O-demycinosyl-12,13-epoxytylosin, (b) compounds wherein Z is di(-lower alkoxy), i.e., the diethyl acetals and dimethylacetals such as 4''-iso-valeryl-12,13-epoxytylosin-20-dimethylacetal, and (c) hydrazone derivatives of, for example, 20-deoxo-20-imino-3-O-acetyl-12,13-oxo-4''-O-iso-valeryltylosin especially those wherein Z is (4,4-dioxothiomorpholinyl)imino, i.e.

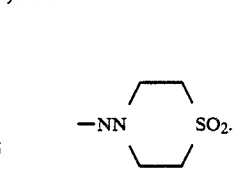

Other useful hydrazones includes those wherein Z is

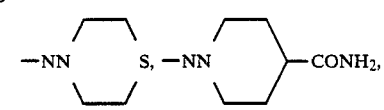

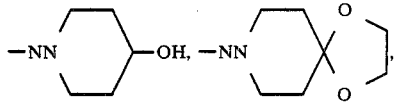

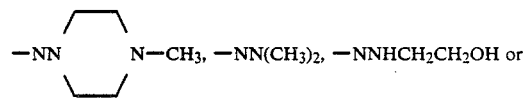

The hydrazone derivatives may be conveniently prepared in accordance with the procedures disclosed in U.S. Pat. No. 4,436,729, Step A of Scheme A at Col. 6, lines 10-29.

The compounds of the present invention may be prepared by oxidation of the 12,13 double bond and formation of the oxirane in the eneone macrolide by using the process disclosed in U.S. Pat. No. 4,477,443 (examples 58–61 on columns 70 to columns 73). The oxidation process begins by reacting a typical suitable starting material, e.g., a 16-membered dienone macrolide such as tylosin, or 4''-O-iso-valeryltylosin, with a suitable reagent to effect protection of any aldehyde groups to prevent such groups from being oxidized to the corresponding carboxylic acid during epoxidation. If aldehyde groups are present, they may be protected in the form of an acetal by dissolving the compound in a mono- or dihydroxy lower alkanol and adding an acid to form the desired acetal.

A peracid, such as m-chloroperbenzoic acid, peroxybenzoic acid or peroxyformic acid is added to, for example, 4''-O-iso-valeryltylosin-20-dimethylacetal; m-chloroperbenzoic acid is the preferred peracid. It is desirable to use an excess of peracid, generally in the range of from about 2 to about 10 equivalents of peracid per equivalent of the 16-membered dienone macrolide; preferably in the range of from about 4 to about 8 equivalents/equivalent.

The reaction proceeds efficiently at room temperature, i.e., 20°–25° C.; the reaction time will be lessened if the epoxidation takes place in a refluxing inert organic solvent such as dichloromethane. Generally, a temperature of from about 0° to 90° C., preferably 25° to 60° C., most preferably 25° to 30° C. is used. The time of reaction will vary considerably from several hours to several days, depending on the specific reactants.

Where acid labile groups, e.g., mycarose, are present in the 16-membered dieneone macrolide, it is preferable to add a mild inorganic base such as disodium hydrogen phosphate, or sodium dihydrogen phosphate to buffer the reaction.

During the epoxidation step, the dimethylamino group in the mycaminosyl sugar moiety present as part of the macrolide molecule will be converted into the N-oxide. The free nitrogen atom of the dimethylamino moiety can be regenerated by reaction with an aromatic phosphine, preferably with triphenylphosphine, or with carbon disulfide. Surprisingly, we have found that, unlike other reducing agents triphenylphosphine and carbon disulfide do not affect either the oxirane ring or the 10,11-double bond in the macrolide molecule.

The protected aldehyde groups may be regenerated by reaction with dilute aqueous organic or mineral acid.

Compounds of this invention containing ($C_2$–$C_7$)alkanoyl (e.g., acetyl, butyryl or iso-valeryl), aryloxy-substituted ($C_2$–$C_7$)alkanoyl, e.g., phenoxyacetyl or lower alkylaroyl group, e.g., toluoyl; aryl($C_2$–$C_7$)alkanoyl, e.g. phenylacetyl at one or more of the 3, 2', 4'', 4''' and 23 positions are particularly desirable. The preferred ($C_2$–$C_7$)alkanoyl group at the 3, 2' and 4''' positions is acetyl. The preferred ($C_2$–$C_7$)alkanoyl groups at the 23 position are acetyl and iso-valeryl. The preferred ($C_2$–$C_7$)alkanoyl group at the 4'' position is iso-valeryl.

A number of substituted 23-O-demycinosyl-12,13-oxo compounds and 12,13-oxo compounds have shown particularly high serum levels, for example, 3,2',23-tri-O-acetyl-23-O-demycinosyl-12,13-oxo-4''-O-iso-valerytylosin and 3-O-acetyl-12,13-oxo-4''-O-iso-valeryltylosin.

The following 4''-O-iso-valeryl substituted 23-O-demycinosyl-12,13-oxo derivatives are expected to show similar properties:
3,2'-di-O-acetyl-23-O-demycinosyl-12,13-epoxy-4''-O-iso-valeryltylosin;
3,23-di-O-acetyl-23-O-demycinosyl-12,13-epoxy-4''-O-iso-valeryltylosin;
3-O-acetyl-23-O-demycinosyl-12,13-epoxy-4''-O-iso-valeryltylosin;
3-O-acetyl-23-O-phenylacetyl-23-O-demycinosyl-12,13-epoxy-4''-O-iso-valeryltylosin; and
23-O-phenylacetyl-23-O-demycinosyl-12,13-epoxy-4''-O-iso-valeryltylosin.

The 23-O-iso-valeryl and 23,4''-di-O-iso-valeryl 12,13-oxo-DMT derivatives also are expected to exhibit similar properties. Other preferred derivatives are the 23-O-phenylacetyl and 23,4''-di-O-phenylacetyl derivatives of 12,13-oxo-DMT. Other preferred tylosin derivatives are:
3,2',4'''-tri-O-acetyl-4''-O-iso-valeryl-12,13-epoxytylosin;
4''-O-n-butyryl-12,13-epoxy-3''-O-n-propionyltylosin; and
4''-O-phenylacetyl-12,13-epoxytylosin.

Other preferred, 12,13-oxo-OMT derivatives are 23-O-iso-valeryl-5-O-mycaminosyltylonolide and 23-O-phenylacetyl-5-O-mycaminosyltylonolide.

These acyl derivatives of the compounds of this invention may be synthesized by acylating the dienone macrolide prior to epoxidation or by acylating the epoxyenone macrolide. The acylation procedures disclosed in our co-pending U.S. patent application, Ser. No. 812,148, filed Dec. 23, 1985, especially Scheme I (at pages 20–22) and Scheme II (at pages 23–24) may be used. As the acylating agent, acid halides and acid anhydrides corresponding to the acyl groups mentioned above are suitable for use in the process. Acetic anhydride is conveniently utilized in the presence of an anhydrous solvent such as dry acetone as the reaction medium at ambient temperatures (20°–30° C.) to effect acylation at the 2'-hydroxy group. Typical reaction times vary from about 10–48 hours, depending upon the nature of the specific reactants employed.

Other acylation procedures may be used. For example, the simultaneous acylation of the 3, 23, 2' and 4'''-hydroxyl groups, if desired, may be conveniently done by the addition of a large molar excess (typically 5–15 equivalents) of the acylating agent and a large molar excess (5–15 equivalents) of a base. Suitable bases are the organic bases such as pyridine, or triethylamine together with 4-dimethylaminopyridine. Solvents include those such as methylene chloride, chloroform and mixtures thereof. Typical reaction times vary from 12–36 hours, while typical temperatures range from about 10°–50° C., with room temperatures being most preferable.

When the selective acylation of the dienone macrolide (prior to epoxidation) or the oxoenone is desirable, the following acylation procedure disclosed in our U.S. patent application Ser. No. 812,148, filed Dec. 23, 1985 is normally used.

Selective Acylation of the 2'-hydroxyl group

The acylation process begins with the introduction of an acyl group at the 2'-hydroxyl position of the 16-membered macrolide. It is necessary to block this hydroxyl group prior to the introduction of any acyl group at the 4''' position. When the acyl group to be introduced at the 4''' position is identical to that of the 2'-acyl group, both may be simultaneously introduced by increasing the molar quantities of the acylating agent and adding a base such as pyridine as a catalyst. The 2'-acyl group is conveniently introduced in the absence of added base to form a reaction mixture. The added base, conveniently triethylamine and an increased amount of the acylating agent for acylating the 4'''-hydroxy group are added to the reaction mixture, without isolation to give 2',4'''-di-O-acyltylosin. Selective acylation of the 2'-hydroxyl group may be carried out by conventional methods known for such acylation of common macrolide antibiotics. The acylation is normally carried out utilizing acetic anhydride in acetone at room temperature for about 24 hours in the absence of added base such as pyridine or triethylamine.

Selective Acylation of the 4'''-hydroxyl croup

The second acylation step, at the 4''' position, is accomplished utilizing the appropriate acid anhydride in the presence of added bases, preferably in the presence of a mixture of pyridine and triethylamine, catalytic amounts (0.02 to 0.1 equivalents) of 4-dimethylaminopyridine and dichloromethane (inert organic solvent) at room temperature for about 2–3 days.

Selective Acylation of the 4''-hydroxyl group

Selective acylation of the 4''-hydroxyl group in tylosin is conveniently accomplished by treating 2',4'''-di-O-acyltylosin with about a stoichiometric amount of the appropriate acylating agent in the presence of more than about 0.1 to about 1 mole of a 4-disubstituted aminopyridine per mole of acylating agent in the presence of added base to produce, for example, 2',4'',4'''-tri-O-acyltylosin (or the corresponding 12,13-oxotylosin derivative) substantially free i.e., containing less than about 1% by weight of 3''-O-acyltylosin such as 2',3",4'''-tri-O-acyltylosin and/or 3-O-acyltylosin such as 3,2',4'''-tri-O-acyltylosin.

When the acylation was conducted with more than a stoichiometric amount (e.g., 1.5 times the stoichiometric amount) of acylating agent (per mole of hydroxyl group), acylation of the 3-hydroxyl occurred as well, especially when higher amounts, e.g., 0.8 to 1.0 moles of the 4-disubstituted aminopyridine per mole of acylating agent were used.

The preferred 4-disubstituted aminopyridine is 4-dimethylaminopyridine (DMAP).

Selective acylation at the 4"-position to provide 2',4",4'''-tri-O-acyltylosin is satisfactorily accomplished using about a stoichiometric amount of the appropriate acylating agent, preferably an acid anhydride in the presence of about 0.2 to about 0.5 moles of DMAP per mole of acylating agent and generally about 2.5 moles of added base (typically triethylamine or pyridine) per mole of acylating agent and an inert organic solvent.

While acid anhydrides are the preferred acylating agents, acid halides may be used if lower reaction temperatures are employed. The preferred acylating agent of the acid anhydrides is iso-valeric anhydride. Typically suitable added bases included tri(loweralkyl)amines, especially triethylamine, pyridine, picoline and piperidine.

Reaction times of about 15-20 hours, normally about 18 hours, are sufficient for complete reaction. Generally, the reaction is carried out in an inert organic solvent such as benzene, toluene, chloroform, dichloromethane, tetrahydrofuran or a mixture of all them together. The temperature range is typically between about −10° and about 50° C., but a higher reaction temperature encourages by-product formation. Generally the preferred reaction temperature is between 10° C. and

Acylation of the 3"-hydroxyl group

Optionally, the 3"-hydroxyl croup can also be acylated during the acylation of the 4"-hydroxyl group. The reagents used to acylate the 4"-hydroxyl may be the same as or different than those used to acylate the 3"-hydroxyl, affording a 2',3",4",4'''-tetra-O-acyl compound. This 3"-hydroxyl group is a tertiary alcohol which reacts only under more severe conditions than those required to acylate the 4"-hydroxyl group. The 3-hydroxyl group must be blocked, preferably as the trimethylsilyl ether derivative, prior to the addition of the 3"-acyl group. Generally, conditions must be more severe, i.e., at higher temperatures, i.e., 60°-100° C., and reaction times somewhat longer. Typically, an acyl chloride is utilized as the acylating agent and tribenzylamine as the basic agent. Any nonpolar, organic solvent is suitable for the conduct of the reaction. Of course, when the 3-position is blocked in a synthetic sequence, it must be deblocked at a later stage after the addition of the 3"-acyl group. Typically this is done after the completion of any convenient later stage in the synthetic sequence.

Selective Acylation of the 3-hydroxyl group

Selective acylation of the 3-hydroxyl group in tylosin is usually accomplished by treating 2',4",4'''-tri-O-acyltylosin (or the corresponding 12,13-oxotylosin derivative) with at least about a stoichiometric amount of the acylating agent in the presence of about 0.5 to about 1.5 moles of a 4-disubstituted aminopyridine per mole of acylating agent in a dry i.e., water-free inert organic solvent as defined above to produce 3,2',4",4'''-tetra-O-acyltylosin substantially free i.e., containing less than about 1% by weight of 3"-O-acyltylosin products such as 3,2',3",4",4'''-penta-O-acyltylosin.

The reaction temperature is typically between −10° and about 50° C., but higher reaction temperatures encourage side-product formation. The preferred acylating agents are acid anhydrides but acid chlorides may be used at low temperatures to avoid side product formation. Use of acid anhydrides at a reaction temperature between 10° and 25° C. is preferred. The preferred 4-disubstituted aminopyridine is 4-dimethylaminopyridine. Generally, the reaction is complete in 20-30 hours at about 25° C.

Acylation of the 3 position to provide a tetra-acyl (or, if the 3" position has been acylated, a pentaacyl) compound is most satisfactorily accomplished utilizing about 1.5 to about 4 moles of the appropriate acid anhydride with about 0.5 to about 1.5 moles, preferably about 1 mole of 4-dimethylaminopyridine, in the presence of about 2.5 moles of externally added base, e.g., triethylamine per mole of acylating agent and dichloromethane at room temperature for about 20-24 hours.

Selective Removal of 2' and 4'''-acyl groups

The 2' and 4'''-acyl groups are selectively removed from tri-O-acyltylosin, e.g., 2',4",4'''-tri-O-acyltylosin and from tetra-O-acyltylosin, e.g., 3,2',4",4'''-tetra-O-acyltylosin (or the corresponding 12,13-oxotylosin derivatives) to form 4"-O-acyltylosin and 3,4"-di-O-acyltylosin substantially free of the side products, i.e., the aldol condensation products formed under acidic and basic conditions and Michael addition products formed under basic condition, encountered by use of prior art deblocking methods. By the term "substantially free" as used herein is meant less than about 1% based on desired product. The selective deacylation step is conveniently accomplished by treating the 3,4',4",4'''-tetra-O-acyltylosin or 2',4",4'''-tri-O-acyltylosin (or the corresponding 12,13-oxotylosin derivatives) with a deblocking reagent comprising an organic trisubstituted nitrogen base, and a lower alkanol at a temperature in the range of about 0° to 60° C. for about 2½ to 3 days.

As used herein, the term "organic trisubstituted nitrogen base" refers to acyclic tertiary amines, pyridine and lower alkyl substituted pyridines and bicyclic tertiary amines. Typical suitable acyclic tertiary aliphatic amines include tri(lower alkyl) amines such as trimethylamine, triethylamine, tri-n-propylamine and dimethyl-sec-butylamine. Triethylamine is the preferred acyclic tertiary amine. Typical suitable substituted pyridines include 2-, 3- and 4-methylpyridine. Typical suitable bicyclic tertiary amines include 1,5-diazabicyclo[4.3.0]-non-5-ene, hereinafter "DBN" and 1,8-diazabicylo[5.4.0]undec-7-ene, hereinafter "DBU".

The 2' and 4'''acyl groups are removed, preferably by utilizing a lower alkanol such as methanol and an organic tri-substituted nitrogen base such as triethylamine at room temperature (about 20°-30° C.) for about 2.5 days. Generally at least about 2 moles and typically about 5 to about 20 moles of the organic tri-substituted nitrogen base per mole of tetra or triacyltylosin (or the corresponding tetra- or triacyl-12,13-oxotylosin) are employed. Sufficient lower alkanol is added to form a solution containing about 1.5 to about 3 weight percent of the organic tri-substituted nitrogen base per volume of lower alkanol. The resulting 3,4"-di-O-acyl tylosin or 3,4"-di-O-acyl-12,13-oxotylosin may then be derivatized, preferably as a hydrazone or it may be used as the starting material for a process for producing 3,4''-di-O-acyl-23-O-demycinosyltylosin (DMT) or 3,4''-di-O-acyl-23-O-demycinosyl-12,13-oxotylosin.

Derivitization of the 12,13-oxomacrolide to the corresponding 20-imino compound is accomplished by reaction of the 12,13-oxo compound with a "1-imino reactant" of the formula $$H_2-Z$$

wherein Z is any of the groups defined above in reference to formula I, except oxygen. Many of the "1-amino reactants" herein utilized are commercially available. Those that must be synthesized may be prepared by one of the procedures found in Biel, et al., J. Org. Chem., 26, 4096 (1961) or Gosl, et al., Org. Syn., Collect., V, 43 (1963). Generally, the reaction is conducted in a nonpolar anhydrous organic solvent such as benzene, toluene, chloroform, dichloromethane, tetrahydrofuran or a mixture thereof. Reaction temperatures range from about 0°–50° C., with room temperature being preferred. Reaction times vary from 12 hours to 10 days, depending upon the reactants employed.

Cleavage

The 3,4''-di-O-acyl-12,13-oxo-23-O-DMT's may be prepared by acylating 3,4''-di-O-acyl-12,13,oxotylosin at the 2' position and then cleaving the mycinose sugar and the 2'-acyl group. The 3,2',4'' tri-O-acyl-12,13-oxo-23O-DMT compounds may also be formed in the same manner. This is accomplished by reacting the 3,2',4'''composition with 1-N-ethyl-3-N-(3-dimethylaminopropyl) carbodiimide HCl and dimethyl sulfoxide in pyridine and trifluoroacetic acid for 1½ to 3 days.

A variety of products are produced depending on the reaction conditions: 3,2',4''-tri-O-acyl-23-O-demycinosyl-12,13-oxotylosin; 3,2',4''-tri-O-acyl-4'''-dehydro-4'''-deoxy-4'''-oxo-12,13-oxotylosin and 3,2',4''-tri-O-acyl-2''',3''',4''-tridehydro-2'''-demethoxy-4'''-deoxy-4'''-oxo-12,13-oxotylosin. The later two compounds will form either 3,4''-di-O-acyl-23-O-demycinosyl-12,13oxotylosin and/or 3,2',4''-tri-O-acyl-23-O-demycinosyl-12,13-oxotylosin by reaction with triethylamine in methanol under appropriate conditions.

Acylation of these compounds at the 23-O-position may then be accomplished by standard methods, most satisfactorily by utilizing the appropriate anhydride in 4-dimethylaminopyridine, and pyridine or triethylamine and dichloromethane at room temperature for 40–48 hours.

This invention also relates to pharmaceutical composition comprising a compound of the invention or its pharmaceutically acceptable acid addition salts in admixture with a pharmaceutically acceptable carrier.

The compounds of the present invention are capable of forming pharmaceutically acceptable acid addition salts with inorganic and organic acids. By "pharmaceutically acceptable acid addition salts" is meant those that do not exhibit toxic manifestations at normal therapeutic doses. Exemplary of such salts are those formed with such acids as hydrochloric, sulfuric, phosphoric, citric, acetic, propionic, tartaric, maleic, benzoic, cyclopropylcarboxylic, adamantylcarboxylic, lauryl sulfonic, glucoheptonic, stearic, lactobionic and the like. Pharmaceutically acceptable acid addition salts may be prepared by methods generally used the art such as by adding a stoichiometric amount of acid to a solution of the antibiotic in an inert organic solvent and isolating the salt by art known methods such as precipitation of the salt with a solvent wherein the salt is not appreciably soluble, e.g. diethyl ether. An inert organic solvent is one which does not react with the antibacterial, the acid or the salt under the conditions of the reaction.

Typical pharmaceutically acceptable carriers suitable for use in the formulations described are exemplified by sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinyl pyrrolidone; polyvinyl alcohol; stearic acid; alkaline earth metal stearates such as magnesium stearate; vegetable oils such as peanut oil, cottonseed oil, sesame oil, olive oil and corn oil; non-ionic, cationic and anionic surfactants, ethylene glycol polymers; betacyclodextrin; fatty acids, hydrolyzed cereal solids; water, polyalkylene glycols; gums; and petroleum; as well as other non-toxic compatible fillers, binders, and lubricants commonly used in pharmaceutical formulations. The compositions may also contain preservatives, areosol propellants and coloring, thickening, suspending, dispensing, emulsifying, wetting, stabilizing and buffering agents.

This invention also embraces a method of treating susceptible bacterial infections in a mammal such as man in need of such treatment which comprises administering to the mammal an antibacterially effective amount of a compound of formula I or a pharmaceutical composition thereof.

In order to treat a susceptible bacterial infection, the compounds of this invention may he administered orally, intramuscularly, topically or intraveneously. Administration may be effected by any of the conventional methods, i.e., by the use of tablets, capsules, and suspensions, solutions, creams, ointments or injectables. Each of the dosage forms can be formulated utilizing non-toxic pharmaceutically acceptable excipients conventionally known in the art. The compounds of this invention are preferably administered at from about 1 to about 500 mg per kg per day, but preferably from about 5 to about 50 mg per kg per day in single or divided doses.

The compounds of this invention exhibit an antibacterial effect against a wide variety of bacterial species, but are generally more active against strains of Gram-positive bacteria. Exemplary of the bacteria against which the compounds of this invention are active are various strains of Staphylococci and Streptococci.

The compounds of the invention, e.g. 12,13oxotylosin have a similar spectrum of antibacterial activity to that of the commercial macrolide, tylosin. The compounds are also active against erythromycin resistant strains of Staphylococci and methicillin-susceptible and methicillin-resistant strains of Staphylococci.

The antibacterial activity of the compounds of this invention is determined by testing against a variety of pathogens using standard antibacterial dilution assays in Mueller-Hinton agar, the activity being expressed as the Minimum Inhibitory Concentration (MIC, mcg./ml., 24 hours). The geometric mean MIC's of the compounds of this invention are in the range of about 0.03 to 4.0.

Most importantly, the compounds of this invention are active antibacterial agents which afford good serum levels at antibacterially effective dosages.

The compounds of the present invention have been found to exhibit serum levels that are superior to those of other macrolides such as erythromycin, rosaramicin, tylosin, and 3-O-acetyl-4''-O-iso-valeryltylosin following oral administration to squirrel monkeys. For example, 3-O-acetyl-12,13-oxo-4''-O-iso-valeryltylosin and 3,23,2'-tri-O-acetyl-23-O-demycinosyl-12,13-oxo-4''-O-iso-valeryltylosin also exhibit superior serum levels to those of 3-O-acetyl-4''-O-iso-valeryltylosin when administered orally to squirrel monkeys. 3,23,2'-Tri-O-acetyl-23-O-demycinosyl-12,13-oxo-4''-O-iso-valeryltylosin has also been found to exhibit higher serum levels when administered intravenously to mice than those of erythromycin, rosaramicin, tylosin, 3-O-acetyl-23-O-demycinosyl-4''-O-iso-valeryltylosin, or 3-O-acetyl-4''-O-iso-valeryltylosin. The compounds of the present invention have a tylosin-like antibacterial spectrum, but are more potent than tylosin.

General Experimental

Optical rotations were recorded at a concentration of 0.3%. Infrared (IR) spectra were recorded on a Perkin-Elmer Infracord 137, or 221 spectrometer, or on a Pye Unicam 3-200 spectrometer. Ultraviolet (UV) spectra were run on a Cary 118 spectrometer. Circulardichroism (CD) spectra were run on a Cary 61 spectrometer. Low resolution EI mass spectra were run on a Varian MAT CH5 spectrometer. Fast Atom Bombardment (FAB) mass spectra (MS) were run on a Finnigan MAT 312 double focussing mass spectrometer, operating at an accelerating voltage of 3 kV. The MS samples were ionized by bombardment with xenon atoms produced by a saddle field ion source from Ion Tech operating with a tube current of 2 mA at an energy of 6 KeV. The proton nuclear magnetic resonance ($^1$H-NMR) spectra were recorded at 79.5 MHz on a Varian CFT-20 spectrometer; at 100 MHz on a Varian XL-100-15 spectrometer; at 200 MHz on a Varian XL-200 spectrometer; and at 400 MHz on a Varian XL-400 spectrometer. All chemicals shift values $\delta$ are reported in ppm downfield from tetramethylsilane.

EXAMPLE 1

12,13-Oxodesmycosin from desmycosin-20-dimethylacetal (a) Desmycosin-20-dimethylacetal:

Tylosin (5 g.) was dissolved in 0.1N hydrogen chloride in methanol (200 ml) and the solution was allowed to remain at 25° C. for 18 h. The reaction was neutralized with Amberlite IRA 401S (OH$^-$) resin and the resin was filtered off and washed with methanol. The combined filtrates were evaporated to dryness and the residue was chromatographed on a silica gel column (100×5 cm.) using 5% methanol in chloroform as the eluant to give desmycosin-20-dimethylacetal (3.53 g., 79%) as a colourless amorphous solid (Anal. found: C, 59.81; H, 8.28; N, 1.59%); $C_{41}H_{70}NO_{15}$ requires: C, 60.28; H, 8.64; N, 1.71%); Rotation: $[\alpha]_D^{26} -0.8°$ (CH$_3$OH); UV: $\lambda_{max}$ (CF$_3$CH$_2$OH) 284 nm ($\epsilon$22,023); IR: $\nu_{max}$ (CDCl$_3$) 3580, 2990, 2960, 2900, 1720, 1685, 1600, 1320, 1190, 1170, 1060 cm$^{-1}$; H$^1$—NMR: $\delta_H$ (CDCl$_3$) 0.93 (3H,t,J$_{16,17}$—CH$_3$ 7 Hz 17-CH$_3$), 1.02 (3H,d,J 7 Hz, CH$_3$), 1.19 (3H,d,J 7 Hz, CH$_3$), 1.27 (3H,d,J 7 Hz, CH$_3$), 1.32 (3H,d,J 7 Hz, CH$_3$), 1.80 (3H,d, J$_{12-CH_3, 13}$) 1.5 Hz, 12-CH$_3$), 2.54 (6H, s, 3'-N(CH$_3$)$_2$), 3.28 (3H,s,20-(OCH$_3$)$_2$), 3.33 (3H,s,20-(OCH$_3$)$_2$), 3.51 (3H,s,2''-OCH$_3$), 3.65 (3H,s,3''-OCH$_3$), 4.34 (1H,d,J$_{1'ax,2'ax}$ 7.5 Hz, H$_{1'ax}$), 4.59 (1H,d,J$_{1''ax,2''ax}$ 8 Hz, H$_{1''ax}$), 5.00 (1H,m,H$_{15}$), 5.90 (1H,dq,J$_{12-CH_3,13}$ 1.5 Hz, J$_{13,14}$ 10 Hz, H$_{13}$), 6.28 (1H,d,J$_{10,11}$ 15 Hz, H$_{10}$) and 7.31 (1H,d,J$_{10,11}$ 15 Hz, H$_{11}$).

(b) 12,13-Oxodesmycosin-20-dimethylacetal-3'-N-oxide

Desmycosin-20-dimethylacetal (3 g) and m-chloroperbenzoic acid (3.81 g) were dissolved in dry dichloromethane (150 ml) and disodium hydrogen phosphate (5.22 g) was added. The resulting suspension was stirred under reflux at 60° C. for 23 hrs. Water was added and the pH was adjusted to 10. The dichloromethane layer was separated, washed with water, dried (MgSO$_4$) and evaporated to dryness. The residue was chromatographed on a silica gel column (60×2.5 cm) using 2% methanol in chloroform as the eluant to give 12,13-oxodesmycosin-20-dimethylacetal-3'-N-oxide (1.42 g, 46%) as a colorless amorphous solid, (Anal. found: C,55.30; H,7.95; N,1.46%. $C_{41}H_{71}NO_{17}\cdot0.3CHCl_3$ requires: C,55.59; H,8.08; N,1.58%); MS: m/z 850 (MH$^+$); Rotation: $[\alpha]_D^{26} -12.4°$ (CHCl$_3$); CD:[O]$_{243}$ −34,741(CH$_3$OH); UV: $\lambda_{max}$(CH$_3$OH) 237 nm ($\epsilon$11,977); IR: $\nu_{max}$(CDCl$_3$) 3570, 3550 3360, 1720, 1692, 1620, 1218, 1170, 1128, 1080, 1070 cm$^{-1}$; H$^1$-NMR: $\delta_H$ (CDCl$_3$) 0.90 (3H,t,J$_{16,17-CH_3}$ 7 Hz, 17-CH$_3$), 1.04 (3H,d,J$_{4,4}$-CH$_3$ 7 Hz,4-CH$_3$), 1.16 (3H,d,J$_{8,8}$-CH$_3$ 7 Hz, 8-CH$_3$), 1.28 (3H,d,J$_{5''ax,6''-CH_3}$ 6.5 Hz, 6''-CH$_3$), 1.38 (3H,d,J$_{5'ax,6'-CH_3}$6.5 Hz, 6'-CH$_3$), 1.45 (3H,s,12-CH$_3$), 3.28 (3H,s,3'-N(CH$_3$)$_2$→O), 3.30 (3H,s,20-(OCH$_3$)$_2$), 3.32 (3H,s,20-(OCH$_3$)$_2$), 3.48 (3H,s,3'-N-(CH$_3$)$_2$→O), 3.58 (3H,s,2''-OCH$_3$), 3.64 (3H,s,3''-OCH$_3$), 4.42 (1H,d,J$_{1'ax,2'ax}$ 7.5 Hz, H$_{1'ax}$), 4.60 (1H,d,J$_{1''ax,2''ax}$ 7.5 Hz, H$_{1''ax}$), 6.45(1H,d,J$_{10,11}$ 16 Hz,H$_{10}$) and 6.60 (1H,d,J$_{10,11}$16Hz,H$_{11}$). Traces of desmycosin-20-dimethylacetal-3'-N-oxide (36 mg, 1%) were also isolated.

(c) 12,13-Oxodesmycosin-20-dimethylacetal 12,13-Oxodesmycosin-20-dimethylacetal-3'-N-oxide (350 mg) and triphenylphosphine (1.08 g) were dissolved in dry dichloromethane (20 ml) and the mixture was refluxed under argon at 55° C. for 67 hours. The solution was evaporated to dryness and the residue was chromatographed on a silica gel column (30×2.5 cm) using initially chloroform and then 2% methanol in chloroform as the eluant to give 12,13-oxodesmycosin-20-dimethylacetal (211 mg, 62%) as a colorless amorphous solid, (Anal. found: C, 57.87; H, 8.24; N, 1.57. $C_{41}H_{71}NO_{16}\cdot 0.2$ CHCl$_3$ requires: C, 57.40; H, 8.34; N, 1.63%); MS: m/z 834 (MH$^+$); Rotation: $[\alpha]_D^{26} -18.0°$ (CHCl$_3$); CD: $[\theta]_{245}$-54,099, $[\theta]_{285}$+2,254, $[\theta]_{335}$−9,017 (CH$_3$OH); UV: $\lambda_{max}$ (CH$_3$OH) 237 nm ($\epsilon$13,840); IR: $\nu_{max}$ (CDCl$_3$) 3540, 3440, 1717, 1688, 1617, 1313, 1187, 1173, 1121, 1060 cm$^{-1}$; H$^1$-NMR: $\delta_H$ (CDCl$_3$) 0.90 (3H, t, J$_{16,17-CH_3}$ 7 Hz, 17-CH$_3$), 1.08 (3H, d, J$_{4,4-CH_3}$ 7 Hz, 4-CH$_3$), 1.16 (3H, d, J$_{8,8-CH_3}$ 6.5 Hz, 8-CH$_3$), 1.28 (3H, d, J$_{5''ax, 6''-CH_3}$ 6.5 Hz, 6''-CH$_3$), 1.32 (3H, d, J$_{5'ax, 6'-CH_3}$6.5 Hz, 6'-CH$_3$), 1.44 (3H, s, 12-CH$_3$), 2.54 (6H, s, 3'-N(CH$_3$)$_2$), 3.26 (3H, s, 20-(OCH$_3$)$_2$), 3.32 (3H, s, 20-(OCH$_3$)$_2$), 3.58 (3H, s, 2''-OCH$_3$), 3.64 (3H, s, 3''-OCH$_3$), 4.36 (1H, d, J$_{1'ax, 2'ax}$7.5 Hz, H$_{1'ax}$), 4.60 (1H, d, J$_{1''ax, 2''ax}$7.5 Hz, H''$_{ax}$), 6.45 (1H, d, J$_{10,11}$ 16 Hz, H$_{10}$) and 6.60 (1H, d, J$_{10,11}$ 16 Hz, H$_{11}$).

(d) 12,13-Oxodesmycosin 12,13-Oxodesmycosin-20-dimethylacetal (617 mg) was dissolved in 0.1N aqueous hydrochloric acid (75 ml) and the solution was allowed to remain at 25° C. for 16 hours. The pH was adjusted to 10 and the aqueous solution was extracted with dichloromethane. The dichloromethane layer was washed with water, dried (MgSO$_4$), filtered and evaporated to dryness. The residue was chromatographed on a silica gel column (30×2.5 cm) using 2% methanol in chloroform as the eluant to give 12,13-oxodesmycosin (302 mg, 52%) as a colorless amorphous solid, (Anal. found: C, 58.69; H, 7.90; N, 1.61. C$_{39}$H$_{65}$NO$_{15}$ . 0.1 CHCl$_3$ requires: C, 58.56; H, 8.19; N, 1.75%); MS: m/z 788 (MH+); Rotation: $[\alpha]_D^{26}$ −33.5° (CHCl$_3$); CD: $[\theta]_{240}$ −114,768, $[\theta]_{280}$ −3,426, $[\theta]_{330}$ −9,421 (CH$_3$OH); UV: $\lambda_{max}$ (CH$_3$OH) 237 nm ($\epsilon$14,910), IR: $\nu_{max}$ (CDCl$_3$) 3515, 1715, 1690, 1618, 1313, 1183, 1163, 1058 cm$^{-1}$; H$^1$-NMR: $\delta_H$(CDCl$_3$) 0.91 (3H, t, J$_{16,17\text{-}CH_3}$ 7 Hz, 17-CH$_3$), 1.08 (3H, d, J$_{4,4\text{-}CH_3}$ 7 Hz, 4-CH$_3$), 1.17 (3H, d, J$_{8,8\text{-}CH_3}$ 7 Hz, 8-CH$_3$), 1.26 (3H,d,J$_{5'ax,6'\text{-}CH_3}$ 7 Hz, 6'CH$_3$), 1.28 (3H, d, J$_{5''ax,6''\text{-}CH_3}$ 7 Hz, 6''-CH$_3$), 1.44 (3H, s, 12-CH$_3$), 2.52 (6H, s, 3'-N(CH$_3$)$_2$), 3.58 (3H, s, 2''-OCH$_3$), 3.64 (3H, s, 3''-OCH$_3$), 4.29 (1H, d, J$_{1'ax, 2'ax}$ 7.5 Hz, H$_{1'ax}$), 4.60 (1H, d, J$_{1'ax, 2'ax}$ 7.5 Hz, H$_{1''ax}$), 6.46 (1H, d, J$_{10,11}$ 15 Hz, H$_{10}$), 6.61 (1H, d, J$_{10,11}$ 15 Hz, H$_{11}$) and 9.73 (1H, s, H$_{20}$).

EXAMPLE 2

12,13-Oxotylosin from tylosin

(a) Tylosin-20-dimethylacetal

Tylosin (5.7 g) was dissolved in dry methanol (714 ml) and difluoroacetic acid (9.8 ml) was added. The mixture was stirred at 25° C. under argon for 67 hours. Triethylamine (27 ml) was added and after 15 minutes the solution was evaporated to dryness. The residue was taken up in dichloromethane and extracted with water, the pH being maintained throughout at 10.7. The dichloromethane layer was washed with water, dried (MgSO$_4$), filtered and evaporated to dryness. The residue was chromatographed on a silica gel column (30×5 cm) using 2% methanol in chloroform as the eluant to give tylosin-20-dimethylacetal (4.64 g, 78%) as a colorless amorphous solid, (Anal. found: C, 57.65; H, 8.15; N 1.34 . C$_{48}$H$_{83}$NO$_{018}$ . 0.3 CHCl$_3$ requires: C, 57.77; H, 8.38; N, 1.40%); MS: m/z 962 (MH+); Rotation: $[\alpha]_D^{26}$ −33.3° (CHCl$_3$); CD: $[\theta]_{226}$+465, $[\theta]_{278}$+102,263 (CH$_3$OH); UV: $\lambda_{max}$ (CH$_3$OH) 282 nm ($\epsilon$20,835); IR: $\nu_{max}$ (CDCl$_3$) 3530, 3460, 1721, 1674, 1590, 1315, 1158, 1050 cm$^{-1}$; H$^1$-NMR: $\delta_H$ (CDCl$_3$) 0.93 (3H, t, J$_{16,17\text{-}CH_3}$ 7 Hz, 17-CH$_3$), 0.99 (3H, d, J$_{4,4\text{-}CH_3}$ 7 Hz, 4-CH$_3$), 1.18 (3H, d, J$_{8,8\text{-}CH_3}$ 7 Hz, 8-CH$_3$), 1.23 (3H, s, 3''-CH$_3$), 1.27 (3H, d, J 7 Hz, CH$_3$), 1.30 (6H, d, J 7 Hz, CH$_3$), 1.79 (3H, d, J$_{12,12\text{-}CH_3}$ 1Hz, 12-CH$_3$), 2.51 (6H, s, 3'-N(CH$_3$)$_2$), 3.25 (3H, s, 20-(OCH$_3$)$_2$), 3.31 (3H, s, 20-(OCH$_3$)$_2$), 3.50 (3H, s, 2''-OCH$_3$), 3.63 (3H, s, 3''-OCH$_3$), 4.27 (1H, d, J$_{1'ax, 2'ax}$ 8 Hz, H$_{1'ax}$), 4.56 (1H, d, J$_{1'''ax, 2'''ax}$ 8 Hz, H$_{1''ax}$), 5.88 (1H, dq, J$_{12,12\text{-}CH_3}$ 1Hz, J$_{13,14}$ 9.5 Hz, H$_{13}$), 6.26 (1H, d, J$_{10,11}$ 15.5 Hz, H$_{10}$) and 7.30 (1H, d, J$_{10,11}$ 15.5 Hz, H$_{11}$) and desmycosin-20-dimethylacetal (1.08 g, 21%).

(b) 12,13-Oxotylosin-20-dimethylacetal-3'-N-oxide

Tylosin-20-dimethylacetal (1.5 g) was dissolved in dry dichloromethane (75 ml) and disodium hydrogen phosphate (3.76 g) was added . m-Chloroperbenzoic acid (2.6 g) was added and the mixture was stirred under dry argon at 25° C. for 8 hours. The reaction mixture was poured into a mixture of dichloromethane (1200 ml) and water at pH 10.95 (100 ml) and the mixture was shaken. The dichloromethane extracts (1×1200 ml; 2×500 ml) were dried (MgSO$_4$), filtered and evaporated to dryness. The residue was chromatographed on a silica gel column (30×2.5 cm) using initially chloroform (300 ml) and then 8% methanol in chloroform as the eluant to give 12,13-oxotylosin-20-dimethylacetal-3'-N-oxide (1.11 g, 72%) as a colorless amorphous solid, (Anal.: found: C, 55.90; H, 7.23; N, 1.20 . C$_{48}$H$_{83}$NO$_{20}$.0.3 CHCl$_3$ requires: C, 55.97; H, 8.12; N, 1.36%); MS: m/z 994 (MH+); CD: $[\theta]_{243}$ −45,191, $[\theta]_{275}$+2,517, $[\theta]_{340}$ −8,809 (CH$_3$OH), UV: $\lambda_{max}$(CH$_3$OH) 236 nm ($\epsilon$12,369); IR: $\nu_{max}$(CDCl$_3$) 3535, 1718, 1690, 1618, 1315, 1162, 1127, 1057 cm$^{-1}$; H$^1$-NMR: $\delta_H$ (CDCl$_3$) 0.89 (3H, t, J$_{16,17\text{-}CH_3}$ 7 Hz, 17-CH$_3$), 1.14 (3H, d, J7 Hz, CH$_3$), 1.15 (3H, d, J7 Hz, CH$_3$), 1.27 (6H, d, J7 Hz, CH$_3$), 1.28 (3H, s, 3''-CH$_3$), 1.42 (3H, s, 12-CH$_3$), 3.26 (3H, s, 20-(OCH$_3$)$_2$), 3.29 (3H, s, 20-(OCH$_3$)$_2$), 3.33 (3H, s, 3'-N(CH$_3$)$_2$→O), 3.57 (3H, s, 2''-OCH$_3$), 3.60 (3H, s, 3'-N(CH$_3$)$_2$→O), 3.64 (3H, s, 3'''-OCH$_3$), 4.48 (1H, d, J$_{1'ax, 2'ax}$ 8 Hz, H$_{1'ax}$), 4.58 (1H, d, J$_{1'''ax, 2'''ax}$ 8 Hz, H$_{1'''ax}$), 6.44 (1H, d, J$_{10,11}$ 16 Hz, H$_{10}$) and 6.57 (1H, d, J$_{10,11}$ 16 Hz, H$_{11}$).

(c) 12,13-Oxotylosin-20-dimethylacetal 12,13-Oxotylosin-20-dimethylacetal-3'-N-oxide (675 mg) and triphenylphosphine (1.78 g) were dissolved in dry dichloromethane (300 ml) and the solution was stirred under dry argon at 25° C. for 49 hours. The solution was evaporated to dryness and the residue was chromatographed on a silica gel column (30×2 cm) using 3% methanol in chloroform as the eluant to give 12,13-oxotylosin-20-dimethylacetal (552 mg, 83%) as an amorphous solid, (Anal.: found: C, 55.41; H, 7.51; N, 1.22 . C$_{48}$H$_{83}$NO$_{19}$ . 0.5 CHCl$_3$ requires: C, 55.55; H, 8.06; N, 1.35%); MS: m/z 978 (MH+); Rotation: $[\alpha]_D^{26}$ −52.7° (CH$_3$OH); CD: $[\theta]_{246}$ −42,428, $[\theta]_{275}$ +4,714, $[\theta]_{340}$ −9,428 (CH$_3$OH); UV: $\lambda_{max}$ (CH$_3$OH) 237 nm ($\epsilon$13,759); IR: $\nu_{max}$ (CDCl$_3$) 3543, 3480, 1720, 1692, 1620, 1318, 1190, 1162, 1128, 1053 cm$^{-1}$; H$^1$-NMR: $\delta_H$ (CDCl$_3$) 0.89 (3H, t, J$_{16,17\text{-}CH_3}$ 7 Hz, 17-CH$_3$), 1.06 (3H, d, J7 Hz, CH$_3$), 1.15 (3H, d, J7 Hz, CH$_3$), 1.24 (3H, s, 3''-CH$_3$), 1.28 (6H, d, J7 Hz, CH$_3$), 1.32 (3H, d, J7 Hz, CH$_3$), 1.44 (3H, s, 12-CH$_3$), 2.51 (6H, s, 3'-N(CH$_3$)$_2$) 3.27 (3H, s, 20-(OCH$_3$)$_2$), 3.32 (3H, s, 20-(OCH$_3$)$_2$), 3.59 (3H, s, 2'''-OCH$_3$), 3.66 (3H, s, 3'''-OCH$_3$), 4.31 (1H, d, J$_{1'ax,2'ax}$ 8 Hz, H$_{1'ax}$), 4.58 (1H, d, J$_{1'''ax, 2'''ax}$ 8 Hz, H$_{1'''ax}$), 6.44 (1H, d, J$_{10,11}$ 16 Hz, H$_{10}$) and 6.58 (1H, d, J$_{10,11}$ 16 Hz, H$_{11}$).

(d) 12,13-Oxotylosin 12,13-Oxotylosin-20-dimethylacetal (250 mg) was dissolved in a mixture of acetonitrile (2.5 ml) and water (20 ml). Difluoroacetic acid (0.4 ml) was added and the mixture was stirred at 25° C. for 1 hour. The solution was poured into a mixture of dichloromethane (400 ml) and water at pH 11.3 (50 ml). The mixture was shaken and the dichloromethane extracts (1×400 ml; 2×200 ml) were dried (MgSO$_4$), filtered and evaporated to dryness. The aqueous phase was stirred overnight with dichloromethane. The dichloromethane was dried (MgSO$_4$), filtered and evaporated to give additional product. The residues were combined and chromatographed on a silica gel column (30×2 cm) using 4% methanol in chloroform as the eluant to give 12,13- oxotylosin (75 mg, 31%) as a colorless amorphous solid, (Anal.: found: C, 56.53; H, 7.84; N, 1.13. $C_{46}H_{77}NO_{18}$ .0.4 $CHCl_3$ requires: C, 56.39; H, 7.92; N, 1.43%); MS: m/z 932 (MH$^+$); Rotation: $[\alpha]_D^{26} - 53.2°$ ($CHCl_3$); CD: $[\theta]_{245}$ −78,069, $[\theta]_{275}$ 0, $[\theta]_{335}$ −9,463 ($CH_3OH$); UV: $\lambda_{max}$ ($CH_3OH$) 237 nm ($\epsilon$13,119); IR: $\epsilon_{max}$ ($CDCl_3$) 3675, 3535, 1718, 1690, 1615, 1158, 1050 cm$^{-1}$; H$^1$-NMR: $\delta_H$ ($CDCl_3$) 0.90 (3H, t, $J_{16,17-CH3}$ 7 Hz, 17-$CH_3$), 1.06 (3H, d, J7 Hz, $CH_3$), 1.17 (3H, d, J7 Hz, $CH_3$), 1.24 (3H, s, 3″-$CH_3$), 1.28 (6H, d, J7 Hz, $CH_3$), 1.30 (3H, d, J7 Hz, $CH_3$), 1.45 (3H, s, 12-$CH_3$), 2.52 (6H, s, 3′-N($CH_3$)$_2$), 3.59 (3H, s, 2‴-$OCH_3$), 3.66 (3H, s, 3‴-$OCH_3$), 4.24 (1H, d, $J_{1'ax, 2'ax}$ 8 Hz, H$_{1'ax}$), 4.58(1H,d, $J_{1'''ax, 2'''ax}$ 8 Hz, H$_{1'''ax}$), 6.46 (1H, d, $J_{10,11}$ 16 Hz, H$_{10}$), 6.61 (1H, d, $J_{10,11}$ 16 Hz, H$_{11}$) and 9.71 (1H, s, H$_{20}$) and 12,13-oxodesmycosin (121 mg; 61%) which was identical with that described earlier.

EXAMPLE 3

12,13-Oxo-4″-O-iso-valeryltosin from 4″-O-iso-valeryltylosin (a) 4″-O-iso-Valeryltylosin: - Follow procedure described in Example 1F of U.S. Pat. No. 4,435,388 (Ganguly et al.)

(b) 4″-O-iso-Valeryltylosin-20-dimethylacetal

4″-O-iso-Valeryltylosin (5 g) was dissolved in dry methanol (600 ml) and difluoroacetic acid (7.87 ml) was added. The mixture was stirred at 25° C. under argon for 90 hours. Triethylamine (30 ml) was added and after 10 minutes the solution was evaporated to dryness. The residue was taken up in dichloromethane and extracted with water, the pH being maintained throughout at 10.7. The dichloromethane layer was washed with water, dried (MgSO$_4$), filtered and evaporated to dryness. The residue was chromatographed on a silica gel column (60×2.5 cm) using 1% methanol in chloroform as the eluant to give 4″-O-iso-valeryltylosin-20-dimethylacetal (4.5 g, 86%) as a colorless amorphous solid, (Anal.: found: C, 59.21; H,8.37; N, 1.21. $C_{53}H_{91}NO_{19}$ .0.2 $CHCl_3$ requires: C, 59.48; H, 8.57; N, 1.31%); MS: m/z 1046 (MH$^{30}$); Rotation: $[\alpha]_D^{26} - 60.3°$ ($CHCl_3$); UV: $\lambda_{max}$ ($CH_3OH$) 282 nm ($\epsilon$21,900); IR: $\nu_{max}$ ($CDCl_3$) 3480, 1725, 1672, 1590, 1315, 1170, 1120, 1050 cm$^{-1}$; H$^1$-NMR: $\delta_H$ ($CDCl_3$) 0.92 (3H, t, $J_{16,17-CH3}$ 7 Hz, 17-$CH_3$), 0.98 (6H, d, J 7Jz, 4″-OCOCH$_2$CH($CH_3$)$_2$), 1.00 (3H, d, J 7 Hz, $CH_3$), 1.11 (3H, s, 3″-$CH_3$), 1.13 (3H, d, J 7 Hz, $CH_3$), 1.18 (3H, d, J 7 Hz, $CH_3$), 1.26 (6H, d, J 7 Hz, $CH_3$), 1.78 (3H, d, $J_{12-CH313}$, 1Hz, 12-$CH_3$), 2.53 (6H, s, 3′-N($CH_3$)$_2$), 3.25 (3H, s, 20-($OCH_3$)$_2$), 3.30 (3H, s, 20-($OCH_3$)$_2$), 3.50 (3H, s, 2‴-$OCH_3$), 3.63 (3H, s, 3‴-$OCH_3$), 4.28 (1H, d, $J_{1'ax, 2'ax}$ 8 Hz, H$_{1'ax}$), 5.89 (1H, dq, $J_{12-CH313}$, 1Hz, $J_{13,14}$ 10 Hz, H$_{13}$), 6.25 (1H, d, $J_{10,11}$ 15.5 Hz H$_{10}$) and 7.30 (1H, d, $J_{10, 11}$ 15.5 Hz, H$_{11}$).

(c)

12,13-Oxo-4″-O-iso-valeryltylosin-20-dimethylacetal-3′-N-oxide

4″-O-iso-Valeryltylosin-20-dimethylacetal (3.18 g) was dissolved in dry dichloromethane (159 ml) and m-chloroperbenzoic acid (5.24 g) was added and the mixture was stirred under dry argon at 25° C. for 4 hours. The reaction mixture was poured into a mixture of dichloromethane and water at pH 10. The dichloromethane extract was washed with water, dried (MgSO$_4$), filtered and evaporated to dryness. The residue was chromatographed on a silica gel column (30×5 cm) using 4% methanol in chloroform as the eluant to give 12,13-oxo-4″-O-iso-valeryltylosin-20-dimethylacetal-3′-N-oxide (2.17 g, 72%) as a colorless amorphous solid, (Anal.: found: C, 56.84; H, 8.26; N 1.10. $C_{53}H_{91}NO_{21}$ .0.3 $CHCl_3$ requires: C, 57.14; H, 8.23; N, 1.26%); MS: m/z 1078 (MH$^{30}$); Rotation: $[\alpha]_D^{26} - 50.6°$ ($CHCl_3$); CD: $[\theta]_{245}$ −42,693, $[\theta]_{275}$ +2,440, $[\theta]_{335}$ −9,758 ($CH_3OH$); UV: $\lambda_{max}$ ($CH_3OH$) 238 nm ($\epsilon$13,180); IR: $\nu_{max}$ ($CDCl_3$) 3675, 3543, 1725, 1687, 1615, 1163, 1123, 1058 cm$^{-1}$; H$^1$-NMR: $\delta_H$ ($CDCl_3$) 0.87 (3H, t, $J_{16,17-CH3}$ 7 Hz, 17-$CH_3$), 0.98 (6H, d, J, 7 Hz, 4″-OCOCH$_2$CH($CH_3$)$_2$), 1.12 (3H, d, J 7 Hz, $CH_3$), 1.14 (3H, d, J 7 Hz, $CH_3$), 1.16 (3H, s, 3″-$CH_3$), 1.26 (3H, d, J 7 Hz, $CH_3$), 1.34 (3H, d, J 7 Hz, $CH_3$), 1.40 (3H, s, 12-$CH_3$), 3.25 (3H, s, 20-($OCH_3$)$_2$), 3.29 (3H, s, 20-($OCH_3$)$_2$), 3.33 (3H, s, 3′-N($CH_3$)$_2$→O), 3.56 (3H, s, 2‴-$OCH_3$), 3.60 (3H, s, 3′-N($CH_3$)$_2$→O), 3.63 (3H, s, 3‴-$OCH_3$), 4.48 (1H, d, $J_{1'ax,2'ax}$ 8 Hz, H$_{1'ax}$), 4.57 (1H, d, $J_{1'''ax,2'''ax}$ 8 Hz, H$_{1'''ax}$), 4.66 (1H, d, $J_4$″ax, 5″ax 10 Hz, H$_4$″$_{ax}$), 6.43 (1H, d, $J_{10,11}$ 16 Hz, H$_{10}$) and 6.57 (1H, d, $J_{10, 11}$ 16 Hz, H$_{11}$).

(d)

12,13-Oxo-4″-O-iso-valeryltylosin-20-dimethylacetal 12,13-Oxo-4″-O-iso-valeryltylosin-20-dimethylacetal-3′-N-oxide (0.5 g) and triphenylphosphine (1.22 g) were dissolved in dry dichloromethane (205 ml) and the solution was stirred under dry argon at 25° C. for 66 hours. The solution was evaporated to dryness and the residue was chromatographed on a silica gel column (60×2 cm.) using 1.25% methanol in chloroform as the eluant to give 12,13-epoxy-4″-O-iso-valeryltylosin-20-dimethylacetal (328 mg. 67%) as a colorless amorphous solid, (Anal.: found: C, 57.95; H, 8.35; N, 1.19. $C_{53}H_{91}NO_{20}$ . 0.3 $CHCl_3$ requires: C, 57.97; H, 8.36; N, 1.28%); MS: m/z 1062 (MH$^{30}$); Rotation: $[\alpha]_D^{26} - 46.9°$ ($CHCl_3$); CD: $[\theta]_{248}$ −7,861, $[\theta]_{275}$ +15,722, $[\theta]_{335}$ −7,861 ($CH_3OH$); UV: $\lambda_{max}$ ($CH_3OH$) 237 nm ($\epsilon$12,262); IR: $\nu_{max}$ ($CDCl_3$) 3675, 3500, 1722, 1618, 1316, 1186, 1160, 1118, 1052 cm$^{-1}$; H$^1$-NMR $\delta_H$ ($CDCl_3$) 0.91 (3H, t, $J_{16,17-CH3}$ 7 Hz, 17-$CH_3$), 0.99 (6H, d, J 7 Hz, 4″-OCOCH$_2$CH($CH_3$)$_2$), 1.09 (3H, d, H 7 Hz, $CH_3$), 1.14 (3H, d, J 7 Hz, $CH_3$), 1.15 (3H, s, 3″-$CH_3$), 1.16 (3H, d, J 7 Hz, $CH_3$) 1.26 (3H, d, J 7 Hz, $CH_3$), 1.28 (3H, d, J 7 Hz, $CH_3$), 1.43 (3H, s, 12-$CH_3$), 2.54 (6H, s, 3′-N($CH_3$)$_2$), 3.25 (3H, s, 20-($OCH_3$)$_2$), 3.30 (3H, s, 20-($OCH_3$)$_2$), 3.58 (3H, s, 2‴-$OCH_3$), 3.64 (3H, s, 3‴-$OCH_3$), 4.32 (1H, d, $J_{1'ax,2'ax}$ 8 Hz, H$_{1'ax}$), 4.59 (1H, d, $J_{1'''ax,2'''ax}$ 7 Hz, H$_{1'''ax}$), 6.46 (1H, d, $J_{10,11}$ 16 Hz, H$_{10}$) and 6.59 (1H, d, $J_{10,11}$ 16 Hz, H$_{11}$).

(e) 12,13-Oxo-4″-O-iso-valeryltylosin 12,13-Oxo-4″-O-iso-valeryltylosin-20-dimethylacetal (178 mg) was dissolved in a mixture of acetonitrile (5.34 ml) and water (11.5 ml). Difluoroacetic acid (0.264 ml) was added and the mixture was stirred at 25° C. for 1 hour. The solution was poured into a mixture of dichloromethane (200 ml) and water at pH 11 (100 ml). The dichloromethane extract was washed with water, dried (MgSO$_4$), filtered and evaporated to dryness. The residue was chromatographed on a silica gel column (30×2 cm.) using 1.75% methanol in chloroform as the eluant to give 12,13-oxo-4″-O-iso-valeryltylosin (94 mg, 55%) as a colorless amorphous solid, (Anal. found: C, 56.84; H, 8.25; N, 1.28. $C_{51}H_{85}NO_{19}$ .0.15 $CHCl_3$ requires: C, 56.94; H, 7.97; N, 1.31%); MS: m/z 1016 (MH$^{30}$); rotation: $[\alpha]_D^{26} - 53.2°$ ($CHCl_3$); CD: $[\theta]_{245}$ −52,301, $[\theta]_{275}$ +7,845, $[\theta]_{330}$ 2,615 ($CH_{30}H$); UV: $\lambda_{max\,(CH_3OH)}$ 238 nm ($\epsilon$13,229); IR: $\nu_{max}$ (CDCl$_3$) 3660, 3450, 1725, 1640, 1620, 1248, 1050 cm$^{-1}$; H$^1$-NMR: $\delta_H$ (CDCl$_3$) 0.90 (3H, t, J$_{16,17\text{-}CH_3}$ 7 Hz, 17-CH$_3$), 0.97 (6H, d, J 7 Hz, 4''-OCOCH$_2$CH(CH$_3$)$_2$), 1.06 (3H, d, J 7 Hz, CH$_3$), 1.11 (3H, s, 3''-CH$_3$), 1.13 (3H, d, J, 7 Hz, CH$_3$), 1.18 (3H, d, J, 7 Hz, CH$_3$), 1.22 (3H, d J 6 Hz, CH$_3$), 1.27 (3H, d, J, 7 Hz, CH$_3$), 1.43 (3H, s, 12-CH$_3$), 2.52 (6H, s, 3'-N(CH$_3$)$_2$), 3.56 (3H, s, 2'''-OCH$_3$), 3.62 (3H, s, 3'''-OCH$_3$), 4.22 (1H, d, J$_{1'ax,2'ax}$ 8 Hz, H$_{1'ax}$), 4.58 (1H, d, J$_{1'''ax,2'''ax}$ 8 Hz, H$_{1'''ax}$), 6.43 (1H, d, J$_{10,11}$ 16 Hz, H10), 6.54 (1H, d, J$_{10,11}$ 16 Hz, H$_{11}$) and 9.66 (1H, s, H$_{20}$).

EXAMPLE 4

3,23,2'-Tri-O-acetyl-23-O-demycinosyl-12,13-oxo-4''-O-iso-valeryltylosin from 3,2',4'''-tri-O-acetyl-12,13-oxo-4''-O-iso-valeryltylosin (a)

3,2',4'''-Tri-O-acetyl-12,13-oxo-4''-O-iso-valeryltylosin 12,13-Oxo-4''-O-iso-valeryltylosin from Example 3(e) (10.9 g), 4-dimethylaminopyridine (2.6 g) and triethylamine (15 ml) were dissolved in dry dichloromethane (300 ml) and acetic anhydride (5.05 ml) was added. The mixture was allowed to remain under dry argon at 25° C. for 18 hours. The mixture was diluted with dichloromethane and extracted with water, the pH being adjusted to 10. The dichloromethane layer was dried (MgSO$_4$), filtered and evaporated to dryness. The residue was triturated with water to remove most of the 4-dimethylaminopyridine and the slurry was filtered. The solid was chromatographed on a silica gel column (30×5 cm.) using 15% acetone in hexane as the eluant to give 3,2',4'''-tri-O-acetyl-12,13-oxo-4''-O-iso-valeryltylosin (9.9 g, 81%) as a colorless amorphous solid, (Anal.: C$_{57}$H$_{91}$NO$_{22}$ requires; C,59.93; H,8.03; N,1.22%; Found: C,59.55; H,7.93; N,1.23%; MS: m/z 1142 (MH$^{30}$); Rotation: [α]$_D^{26}$ −53.1° (CHCl$_3$); CD: [θ]$_{220}$ −63,461 [θ]$_{280}$ +5,769, (CH$_3$OH); UV: $\lambda_{max}$ (CF$_3$CH$_2$OH) 237 nm ($\epsilon$14,276); IR: $\nu_{max}$(CDCl$_3$) 3500, 1738, 1690, 1620, 1238, 1163, 1053 cm$^{-1}$; H$^1$-NMR: $\delta_H$ (CDCl$_3$) 0.85 (3H, t, J$_{16\ 17\text{-}CH_3}$ 7 Hz, 17-CH$_3$), 0.98 (6H, d, J 7 Hz, 4''-OCOCH$_2$CH(CH$_3$)$_2$), 1.04 (3H, d, J 7 Hz, CH$_3$), 1.12 (3H, s, 3''-CH$_3$), 1.14 (3H, d, J 7 Hz, CH$_3$), 1.18 (3H, d, J 7 Hz, CH$_3$), 1.21 (3H, d, J 7 Hz, CH$_3$), 1.48 (3H, s, 12-CH$_3$), 2.07 (3H, s, 3-OCOCH$_3$), 2.09 (3H, s, 2'-OCOCH$_3$), 2.12 (3H, s, 4'''-OCOCH$_3$), 2.41 (6H, s, 3'-N(CH$_3$)$_2$), 3.54 (6H, s, 2'''and 3'''-OCH$_3$), 4.28 (1H, d, J$_{1'ax,2'ax}$ 8 Hz, (H$_{1'ax}$), 4.64 (1H, d, J$_{1'''ax,2'''ax}$ 8 Hz, H$_{1'''ax}$), 6.53 (1H, d, J$_{10,11}$ 16 Hz, H$_{10}$), 6.72 (1H, d, J$_{10,11}$ 16 Hz, H$_{11}$) and 9.62 (1H, s, H$_{20}$).

(b) 3-O-Acetyl-12,13-oxo-4''-O-iso-valeryltylosin 3,2',4'''-Tri-O-acetyl-12,13-oxo-4''-O-iso-valeryltylosin (10.4 g) and triethylamine (25.5 ml) were dissolved in methanol (1280 ml) and the solution was allowed to stand at 25° C. for 82 hours. The solution was evaporated to dryness and the residue was chromatographed by preparative hplc on a Waters Prep 500 instrument (one silica gel cartridge) using 1.5% methanol in chloroform as the eluant to give 3-O-acetyl-12,13-oxo-4''-O-iso-valeryltylosin (9.4 g, 84%) as a colorless amorphous solid, (Anal.: C$_{53}$H$_{87}$NO$_{20}$.0.2 CHCl$_3$ requires: C,58.82; H,1.29%; Found: C,58.83; H,8.21, N,1.23%); MS: m/z 1058 (MH$^{30}$); Rotation: [α]$_D^{26}$−52.2° (CHCl$_3$); CD: [θ]$_{210}$+78,587, [θ]$_{246}$ −36,674, [θ9$_{303}$ +5,239 (CH$_3$OH); UV: $\lambda_{max}$ (CH$_3$OH) 237 nm, ($\epsilon$11,212); IR: $\nu_{max}$ (CDCl$_3$) 3505, 1730, 1693, 1622, 1163, 1053 cm$^{-1}$; H$^1$-NMR: $\delta_H$(CDCl$_3$) 0.87 (3H, t, J$_{16,17\text{-}CH_3}$ 7 Hz, 17-CH$_3$), 0.98 (6H, d, J 7 Hz, 4''-OCOCH$_2$CH(CH$_3$)$_2$), 1.12 (3H, s, 3''-CH$_3$), 1.14 (3H, d, J 7 Hz, CH$_3$), 1.21 (3H, d, J 7 Hz, CH$_3$), 1.24 (3H, d, J 7 Hz, CH$_3$), 1.27 (3H, d, J 7 Hz, CH$_3$), 1.49 (3H, s, 12-CH$_3$), 2.12 (3H, s, 3-OCOCH$_3$), 2.52 (6H, s, 3'-N(CH$_3$)$_2$), 3.56 (3H, s, 2'''-OCH$_3$), 3.63 (3H, s, 3'''-OCH$_3$), 4.61 (1H, d, J$_{1'ax,2'ax}$ 8 Hz, H$_{1'ax}$), 4.66 (1H, d, J$_{1'''ax,2'''ax}$ 8 Hz, H$_{1'''ax}$), 6.52 (1H, d, J$_{10,11}$ 16 Hz, H$_{10}$), 6.73 (1H, d, J$_{10,11}$ 16 Hz, H$_{11}$), and 9.64 (1H, s, H$_{20}$).

(c) 3,2'-Di-O-acetyl-12,13-oxo-4''-O-iso-valeryltylosin

3-O-Acetyl-12,13-oxo-4''-O-iso-valeryltylosin (8.83 g) was dissolved in dry acetone (530 ml) and acetic anhydride (4 ml) was added. The mixture was allowed to remain under dry argon at 25° C. for 44 hours. The solution was evaporated to dryness and the residue was taken up in dichloromethane and washed with water, the pH being adjusted to 10. The organic layer was dried (MgSO$_4$), filtered and evaporated to dryness. The residue was chromatographed on a silica gel column (30×5 cm.) using 15% acetone in chloroform as the eluant to give 3,2'-di-O-acetyl-12,13-oxo-4''-O-iso-valeryltylosin (7.34 g, 86%) as a colorless amorphous solid, (Anal.: C$_{55}$H$_{89}$NO$_2$ . 0.3 CHCl$_3$ requires: C,58.15; H,7.90; N,1.24%, Found: C,58.21; H,7.90, N,1.03%); MS: m/z 1100 (MH$^{30}$); Rotation: [α]$_D^{26}$ −62.1° (CHCl$_3$); CD: [θ]$_{223}$ −82,112, (CH$_3$OH); UV: $\lambda_{max}$ (CF$_3$CH$_2$OH) 238 nm, ($\epsilon$11,587); IR: $\nu_{max}$ (CDCl$_3$) 3510, 1735, 1710, 1635, 1250, 1180, 1070, 1040 cm$^{-1}$; H$^1$-NMR: $\delta_H$ (CDCl$_3$) 0.87 (3H, t, J$_{16,17\text{-}CH_3}$ 7 Hz, 17-CH$_3$), 0.99 (3H, d, J 7 Hz, 4''-OCOCH$_2$CH(CH$_3$)$_2$), 1.05 (3H, d, J 7 Hz CH$_3$), 1.12 (3H, s, 3''-CH$_3$), 1.14 (3H, d, J 7 Hz, CH$_3$), 1.21 (3H, d, J 7 Hz, CH$_3$), 1.24 (3H, d, J 7 Hz, CH$_3$), 1.27 (3H, d, J 7 Hz, CH$_3$), 1.49 (3H,s,12-CH$_3$), 2.08 (3H, s, 2'-OCOCH$_3$), 2.11 (3H, s, 3-OCOCH$_3$), 2.42 (6H, s, 3'-N(CH$_3$)$_2$), 3.57 (3H, s, 2'''-OCH$_3$), 3.64 (3H, s, 3'''-OCH$_3$), 4.61 (1H, d, J$_{1'ax,2'ax}$ 7.5 Hz, H$_{1'ax}$), 4.66 (1H, d, J$_{1'''ax,2'''ax}$ 8.5 Hz, H$_{1'''ax}$), 6.53 (1H, d, J$_{10,11}$ 16 Hz, H$_{10}$), 6.73 (1H, d, J$_{10,11}$ 16 Hz, H$_{11}$),and 9.63 (1H, s, H$_{20}$).

(d)

3-O-Acetyl-23-O-demycinosyl-12,13-oxo-4''-O-iso-valeryltylosin 3,2'-Di-O-acetyl-12,13-oxo-4''-O-iso-valeryltylosin) and 1-N-ethyl-3-N-(3-dimethylaminopropyl)carbodiimide hydrochloride (1.04 g) were dissolved in dry dimethylsulfoxide (1.66 ml). The solution was stirred under argon at 25° C. and a mixture of pyridine (0.1468 ml) and trifluoroacetic acid (0.06984 ml) in dry dimethylsulfoxide (0.657 ml) was added. The mixture was stirred at 25° C. for 19 hours. The solution was evaporated to dryness under high vacuum and the residue was taken up in dichloromethane and washed with water, the pH being adjusted to 10. The organic layer was dried (MgSO$_4$), filtered and evaporated to dryness. The residue was taken up in methanol (70 ml) containing triethylamine (1.412 ml) and the mixture was allowed to remain at 25° C. for 61 hours. The solution was evaporated to dryness at 30° C. under high vacuum. The residue was chromatographed on a silica gel column (15×5 cm) using 10% acetone in chloroform as the eluant to give 3-O-acetyl-23-O-demycinosyl-12,13-oxo-4''-O-iso-valeryltylosin (264 mg, 66%) as a colorless amorphous solid, (Anal. Found: C,60.99; H,8.32; N,1.30%; C$_{45}$H$_{73}$NO$_{16}$ requires: C,61.14; H,8.32; N,1.58%); MS: m/z 884 (MH$^{30}$); Rotation: [α]$_D^{26}$−50.4° (CHCl$_3$); CD: [θ]$_{218}$ +62,851,

[θ]$_{247}$ −20,950, [θ]$_{281}$ +6,285 (CH$_3$OH); UV: λ$_{max}$ (CH$_3$OH) 238 nm, (ε10,289); IR: λ$_{max}$ (CDCl$_3$) 3580, 3480, 1725, 1690, 1620, 1236, 1160, 1115, 1050, 1022 cm$^{-1}$; H$^1$-NMR: δ$_H$ (CDCl$_3$) 0.91 (3H, t, J$_{16,17\text{-}CH3}$ 7 Hz, 17-CH$_3$), 0.99 (6H, d, J 7 Hz, 4″-OCOCH$_2$CH(CH$_3$)$_2$), 1.13 (3H, s, 3″-CH$_3$), 1.14 (3H, d, J 7 Hz, CH$_3$), 1.16 (3H, d, J 7 Hz, CH$_3$), 1.23 (3H, d, J 7 Hz, CH$_3$), 1.27 (3H, d, J 7 Hz, CH$_3$), 1.52 (3H, s, 12-CH$_3$), 2.17 (3H, s, 3-OCOCH$_3$), 2.53 (6H, s, 3′-N(CH$_3$)$_2$), 4.24 (1H, d, J$_{1'ax,2'ax}$ 8.5 Hz, H$_{1'ax}$), 6.54 (1H, d, J$_{10,11}$ 16 Hz, H$_{10}$), 6.75 (1H, d, J$_{10,11}$ 16 Hz, H$_{11}$), and 9.65 (1H, s, H$_{20}$).

(e)
3,23,2′-Tri-O-acetyl-23-O-demycinosyl-12,13-oxo-4″-O-iso-valeryltylosin

3-O-Acetyl-23-O-demycinosyl-12,13-oxo-4″-O-iso-valeryltylosin (519 mg), 4-dimethylaminopyridine (14.3 mg), pyridine (0.463 ml) and acetic anhydride (0.27 ml) were dissolved in dry dichloromethane (86.5 ml) and the mixture was stirred under argon at 25° C. for 22 hours. The mixture was diluted with dichloromethane and water and the pH was adjusted to 10. The dichloromethane extract was dried (MgSO$_4$), filtered and evaporated to dryness. The residue was chromatographed on a silica gel column (30×2 cm) using 16% acetone in hexane as the eluant to give 3,23,2′-tri-O-acetyl-23-O-demycinosyl-12,13-oxo-4″-O-iso-valeryltylosin (502 mg, 88%) as a colorless amorphous solid, (Anal.: C$_{49}$H$_{77}$NO$_{18}$.0.2 CHCl$_3$ requires: C,59.33; H,7.82; N,1.41%; Found: C,59.45; H,7.96, N,1.35%); MS: m/z 968 (MH$^{30}$); Rotation: [α]$_D^{26}$ −39.7° (CHCl$_3$); CD: [θ]$_{222}$ +71,341, [θ]$_{248}$ −20,383, [θ]$_{278}$ +7,644 (CH$_3$OH); UV: λ$_{max}$ (CH$_3$OH) 239 nm, (ε11,925), 285 nm (ε2,082); IR: λ$_{max}$ (CDCl$_3$) 3490, 1735, 1690, 1620, 1233, 1158, 1048, 1020 cm$^{-1}$; H$^1$-NMR: δ$_H$ (CDCl$_3$) 0.88 (3H, t, J$_{16,17\text{-}CH3}$ 7 Hz, 17-CH$_3$), 0.99 (6H, d, J 7 Hz, 4″-OCOCH$_2$CH(CH$_3$)$_2$), 1.07 (3H, d, J 7 Hz, CH$_3$), 1.13 (3H, s, 3″-CH$_3$), 1.16 (3H, d, J 7 Hz, CH$_3$) 1.22 (3H, d, J 7 Hz, CH$_3$), 1.24 (3H, d, J 6 Hz, CH$_3$), 1.49 (3H, s, 12-CH$_3$), 2.08 (3H, s, 2′-OCOCH$_3$), 2.11 (3H, s, 3-OCOCH$_3$), 2.17 (3H, s, 23-OCOCH$_3$) 2.42 (6H, s, 3′-N(CH$_3$)$_2$), 4.67 (1H, d, J$_{1'ax,2'ax}$ 9 Hz, H$_{1'ax}$), 6.56 (1H, d, J$_{10,11}$ 16 Hz, H$_{10}$), 6.74 (1H, d, J$_{10,11}$ 16 Hz, H$_{11}$), and 9.64 (1H, s, H$_{20}$).

EXAMPLE 5

3,2′-Di-O-Acetyl-23-O-Demycinosyl-12,13-oxo-4″-O-iso-valeryltylosin

Follow the procedure of Example 4(c) except substitute an equivalent quantity of 3-O-acetyl-23-O-demycinosyl-12,13-oxo-4″-O-iso-valeryltylosin (from Example 4(d)) for 3-O-acetyl-12,13-oxo-4″-O-iso-valeryltylosin, and let the reaction go for 17 hours.

EXAMPLE 6

3,23-Di-O-acetyl-23-O-demycinosyl-12,13-oxo-4″-O-iso-valeryltylosin

Follow the procedure of Example 4(b) except substitute an equivalent quantity of 3,23,2′-tri-O-acetyl-23-O-demycinosyl-12,13-oxo-4″-O-iso-valeryltylosin (from Example 4(e)) for 3,2′,4‴-tri-O-acetyl-12,13-oxo-4″-O-iso-valeryltylosin. Heat the solution at 40° C. for about 40 h. to give 3,23-di-O-acetyl-23-O-demycinosyl-12,13-oxo-4″-O-iso-valeryltylosin.

EXAMPLE 7

3-O-Acetyl-23-O-demycinosyl-12,13-oxo-4″-O-iso-valeryl-23-O-phenylacetyltylosin from 3,2′-di-O-acetyl-23-O-demycinosyl-12,13-oxo-4″-O-iso-valeryltylosin (a)
3,2′-Di-O-acetyl-23-O-demycinosyl-12,13-oxo-4″-O-iso-valeryl-23-O-phenylacetyltylosin Follow the procedure of Example 4(e) except substitute an equivalent quantity of phenylacetyl chloride for acetic anhydride.

(b)
3-O-Acetyl-23-O-demycinosyl-12,13-oxo-4″-O-iso-valeryl-23-O-phenylacetyltylosin Follow the procedure of Example 6 except substitute an equivalent quantity of 3,2′-di-O-acetyl-23-O-demycinosyl-12,13-oxo-4″-O-iso-valeryl-23-O-phenylacetyltylosin for 3,23,2′-tri-O-acetyl-23-O-demycinosyl-12,13-oxo-4″-O-iso-valeryltylosin.

EXAMPLE 8

23-O-Demycinosyl-12,13-Oxo-23-O-phenylacetyl-tylosin from 23-O-demycinosyl-23-O-phenylacetyltylosin (a)
23-O-Demycinosyl-23-O-phenylacetyltylosin-20-dimethylacetal Follow the procedure of Example 2(a) except substitute an equivalent quantity of 23-O-demycinosyl-23-O-phenylacetyltylosin for tylosin.

(b)
23-O-Demycinosyl-12,13-oxo-23-O-phenylacetyltylosin-20-dimethylacetal-3′-N-oxide Follow the procedure of Example 2(b) except substitute an equivalent quantity of 23-O-demycinosyl-23-O-phenylacetyltylosin-20-dimethylacetal for tylosin-20-dimethylacetal.

(c)
23-O-Demycinosyl-12,13-oxo-23-O-phenylacetyltylosin-20-dimethylacetal

Follow the procedure of Example 2(c) except substitute an equivalent quantity of 23-O-demycinosyl-12,13-oxo-23-O-phenylacetyltylosin-20-dimethylacetal-3′-N-oxide for 12,13-oxotylosin-20-dimethylacetal-3′-N-oxide.

(d) 23-O-Demycinosyl-12,13-oxo-23-O-phenyl acetyltylosin

Follow the procedure of Example 2(d) except substitute an equivalent quantity of 23-O-demycinosyl-12,13-oxo-23-O-phenylacetyltylosin-20-dimethylacetal for 12,13-oxotylosin-20-dimethylacetal.

EXAMPLE 9

23-O-Demycinosyl-23,4″-di-O-phenylacetyl-12,13-oxotylosin from 23-O-demycinosyl-23-O-phenylacetyltylosin

(a) 2′-O-Acetyl-23-O-demycinosyl-23-O-phenylacetyltylosin

Follow the procedure of Example 4(c) except substitute an equivalent quantity of 23-O-demycinosyl-23-O-phenylacetyltylosin for 3-O-acetyl-12,13-oxo-4″-O-isovaleryltylosin.

(b) 2′-O-Acetyl-23-O-demycinosyl-23,4″-di-O-phenylacetyltylosin

Follow the procedure of Example 1c described in U.S. Pat. No. 4,436,727 except substitute an equivalent quantity of 2′-O-acetyl-23-O-demycinosyl-23-O-phenylacetyltylosin for 2′-O-acetyl-4‴-O-tert-butyldimethylsilyltylosin.

(c) 23-O-Demycinosyl-23,4″-di-O-phenylacetyltylosin

Follow the procedure of Example 6 except substitute an equivalent quantity of 2′-O-acetyl-23-O-demycinosyl-23,4″-di-O-phenylacetyltylosin for 3,23,2′-tri-O-acetyl-23-O-demycinosyl-12,13-oxo-4″-O-iso-valeryltylosin.

(d) 23-O-Demycinosyl-23,4″-di-O-phenylacetyltylosin-20-dimethylacetal

Follow the procedure of Example 2(a) except substitute an equivalent quantity of 23-O-demycinosyl-4″-di-O-phenylacetyltylosin for tylosin.

(e) 23-O-Demycinosyl-23,4″-di-O-phenylacetyl-12,13-oxotylosin-20-dimethylacetal-3′-N-oxide Follow the procedure of Example 2(b) except substitute an equivalent quantity of 23-O-demycinosyl-23,4″-di-O-phenylacetyltylosin-20-dimethylacetal for tylosin-20-dimethylacetal.

(f) 23-O-Demycinosyl-23,4″-di-O-phenylacetyl-12,13-oxotylosin-20-dimethylacetal Follow the procedure of Example 2(c) except substitute an equivalent quantity of 23-O-demycinosyl-23,4″-di-O-phenylacetyl-12,13-oxotylosin-20-dimethylacetal-3′-N-oxide for 12,13-oxotylosin-20-dimethylacetal-3′-N-oxide.

(g) 23-O-Demycinosyl-23,4″-di-O-phenylacetyl-12,13-oxotylosin

Follow the procedure of Example 2(d) except substitute an equivalent quantity of 23-O-demycinosyl-23,4″-di-O-phenylacetyl-12,13-oxotylosin-20-dimethylacetal for 12,13-oxotylosin-20-dimethylacetal.

EXAMPLE 10

23-O-Demycinosyl-12,13-oxotylosin from 23-O-demycinosyltylosin

(a) 23-O-Demycinosyltylosin-20-dimethylacetal

Follow the procedure of Example 2(a) except substitute an equivalent quantity of 23-O-demycinosyltylosin (prepared and described in Example 4(d) of U.S. Pat. No. 4,436,729) for tylosin.

(b) 23-O-Demycinosyl-12,13-oxotylosin-20-dimethylacetal-3′-N-oxide

Follow the procedure of Example 2(b) except substitute an equivalent quantity of 23-O-demycinosyltylosin-20-dimethylacetal for 12,13-epoxytylosin-20-dimethylacetal.

(c) 23-O-Demycinosyl-12,13-epoxytylosin-20-dimethylacetal

Follow the procedure of Example 2(c) except substitute an equivalent quantity of 23-O-demycinosyl-12,13-oxotylosin-20-dimethylacetal-3′-N-oxide for 12,13-oxotylosin-20-dimethylacetal-3′-N-oxide.

(d) 23-O-Demycinosyl-12,13-oxotylosin

Follow the procedure of Example 2(d) except substitute an equivalent quantity of 23-O-demycinosyl-12,13-oxotylosin-20-dimethylacetal for 12,13-oxotylosin-20-dimethylacetal.

We claim:

1. A compound having the formula I

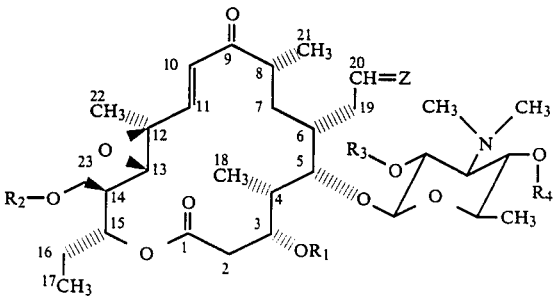

wherein
$R_1$ = ($C_2$–$C_7$) alkanoyl; or ($C_2$–$C_7$) alkanoyl substituted by chloro, lower alkoxy, phenyl, biphenyl, phenoxy or biphenoxy; or benzoyl or phenylbenzoyl; or benzoyl or phenylbenzoyl or phenoxy or biphenoxy substituted by one or more of halogen, nitro, lower alkoxy, or lower alkyl;

$R_2$ = ($C_2$–$C_7$) alkanoyl; or ($C_2$–$C_7$) alkanoyl substituted by chloro, lower alkoxy, phenyl, biphenyl, phenoxy or biphenoxy; or benzoyl or phenylbenzoyl; or benzoyl or phenylbenzoyl or phenoxy or biphenoxy substituted by one or more of halogen, nitro, lower alkoxy, or lower alkyl; or

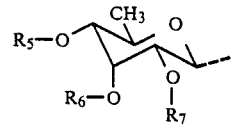

$R_3$ = H or ($C_2$–$C_7$) alkanoyl; or ($C_2$–$C_7$) alkanoyl substituted by chloro, lower alkoxy, phenyl, biphenyl, phenoxy or biphenoxy; or benzoyl or phenylbenzoyl; or benzoyl or phenylbenzoyl or phenoxy or biphenoxy substituted by one or more of halogen, nitro, lower alkoxy, or lower alkyl;

$R_4$=($C_2$-$C_7$) alkanoyl; or ($C_2$-$C_7$) alkanoyl substituted by chloro, lower alkoxy, phenyl, biphenyl, phenoxy or biphenoxy; or benzoyl or phenylbenzoyl; or benzoyl or phenylbenzoyl or phenoxy or biphenoxy substituted by one or more of halogen, nitro, lower alkoxy, or lower alkyl or

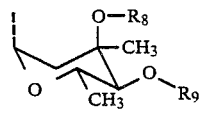

$R_5$=H or ($C_2$-$C_7$) alkanoyl; or ($C_2$-$C_7$) alkanoyl substituted by chloro, lower alkoxy, phenyl, biphenyl, phenoxy or biphenoxy; or benzoyl or phenylbenzoyl; or benzoyl or phenylbenzoyl or phenoxy or biphenoxy substituted by one or more of halogen, nitro, lower alkoxy, or lower alkyl;

$R_6$ is H or methyl and $R_7$ is methyl;

$R_8$ is H or ($C_2$-$C_7$) alkanoyl; or ($C_2$-$C_7$) alkanoyl substituted by chloro, lower alkoxy, phenyl, biphenyl, phenoxy or biphenoxy; or benzoyl or phenylbenzoyl; or benzoyl or phenylbenzoyl or phenoxy or biphenoxy substituted by one or more of halogen, nitro, lower alkoxy, or lower alkyl;

$R_9$ is ($C_2$-$C_7$) alkanoyl; or ($C_2$-$C_7$) alkanoyl substituted by chloro, lower alkoxy, phenyl, biphenyl, phenoxy or biphenoxy; or benzoyl or phenylbenzoyl; or benzoyl or phenylbenzoyl or phenoxy or biphenoxy substituted by one or more of halogen, nitro, lower alkoxy, or lower alkyl;

Z is oxygen, dimethoxy $$=NNH-aralkyl, =NNHCNH_2, =NNHCNH_2 \text{ or}$$
$$\quad\quad\quad\quad\quad\quad\quad\overset{\|}{O}\quad\quad\quad\overset{\|}{S}$$

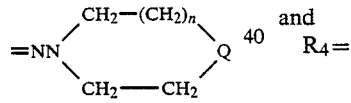

wherein n is 0, 1 or 2 and Q is $CR_{10}R_{11}$, $NR_{10}$, oxygen, S, $SO_2$, $CR_{10}OR_{11}$, $$\begin{matrix} O- \\ C \\ O- \end{matrix} \Big] CR_{10}-O-\overset{O}{\underset{\|}{C}}-R_{11}, CHCOR_{10} \text{ or}$$

$$CH-\overset{O}{\underset{\|}{C}}NR_{10}R_{11},$$

wherein $R_{10}$ and lower alkyl, aralkyl, $R_{11}$ are independently hydrogen, lower alkyl, aralkyl, X-substituted aralkyl, aryl and X-substituted aryl wherein X is independently halogen, trifluoromethyl, lower alkoxy or ($C_2$-$C_7$)alkanoyl; and wherein aryl is substituted by phenyl or biphenyl;

or a pharmaceutically acceptable acid addition salt thereof.

2. The compound of claim 1 wherein
$R_1$=$R_3$=acetyl,
$R_2$=

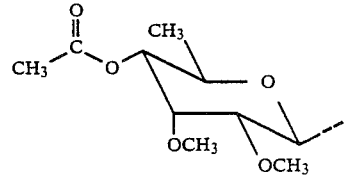

and
Z is oxygen,
$R_4$=

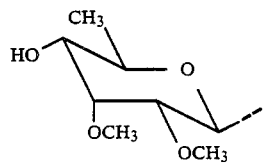

which is 3,2',4'''-tri-O-acetyl-4''-O-iso-valeryl-12,13-oxotylosin.

3. The compound of claim 1 wherein
$R_1$=acetyl; $R_3$=H,
Z is oxygen;
$R_2$=

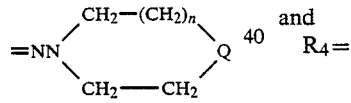

and
$R_4$=

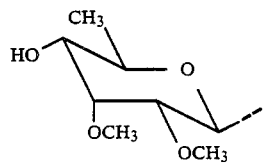

which is 3-O-acetyl-4''-O-iso-valeryl-12,13-oxotyloxin.

4. The compound of claim 1 wherein
$R_1$=$R_3$=acetyl,
Z is oxygen,
$R_2$=

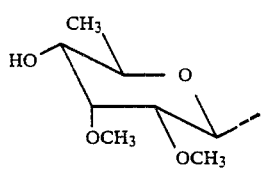

and
$R_4$=

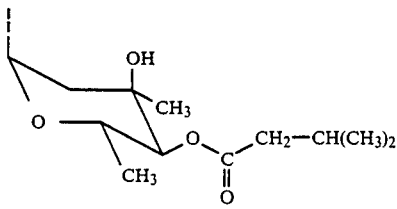

which is 3,2'-di-O-acetyl-4''-O-iso-valeryl-12,13-oxotylosin.

5. The compound of claim 1 wherein
$R_1 = R_2 = R_3 =$ acetyl;
z = oxygen;
$R_4 =$

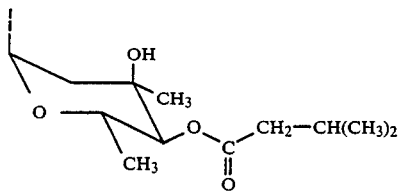

Z is oxygen which is, 3,23,2'-tri-O-acetyl-23-O-acetyl-23-O-demycinosyl-12,13-oxo-4''-iso-valeryl-tylosin.

6. The compound of claim 1 wherein
$R_1 = R_2 =$ acetyl;
$R_3 =$ H;
Z is oxygen;
$R_4 =$

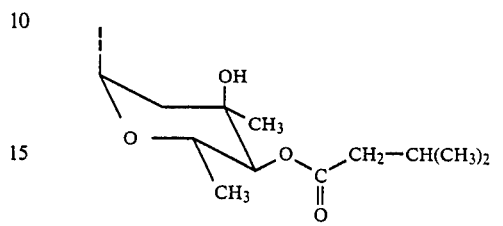

which is 3,23-di-O-acetyl-23-O-demycinosyl-12,13-oxo-4''-O-iso-valeryltylosin.

7. A compound of claim 1 wherein $R_2$ is ($C_2$–$C_7$) alkanoyl; or ($C_2$–$C_7$) alkanoyl substituted by chloro, lower alkoxy, phenyl, biphenyl, phenoxy or biphenoxy; or benzoyl or phenylbenzoyl; or benzoyl or phenylbenzoyl or phenoxy or biphenoxy substituted by one or more of halogen, nitro, lower alkoxy, or lower alkyl.

8. A compound of claim 1 wherein $R_4$ is

TABLE 21

Variation of the content of fractions of neutral lipoids in human blood serum of patients consumed a 40% solution of ethanol (in % of the total lipoids, M ± m) with the composition of this invention

| NN 1 | Fractions 2 | Group I ||| Group II ||
|---|---|---|---|---|---|---|
| | | background 3 | 1 hour 4 | 2 hours 5 | 4 hours 6 | background 7 | 1 hour 8 |
| 1. | Cholesterol esters | 24.35 ± 2.04 | 23.91 ± 0.67 | 22.04 ± 0.41 | 21.53 ± 0.68 | 22.30 ± 1.01 | 24.32 ± 0.55 |
| | % of variation | | 98 | 91 | 88 | | 109 |
| 2. | Triglycerides | 16.41 ± 0.71 | 18.14 ± 0.30 | 18.48 ± 1.24 | 19.51 ± 0.69[1] | 19.95 ± 1.71 | 18.15 ± 0.55 |
| | % of variation | | 111 | 113 | 119 | | 91 |
| 3. | Free fatty acids | 15.96 ± 0.76 | 16.19 ± 0.57 | 16.30 ± 0.26 | 15.90 ± 0.24 | 16.12 ± 0.46 | 16.17 ± 1.10 |
| | % of variation | | 101 | 102 | 106 | | 100 |
| 4. | Cholesterol | 19.21 ± 0.86 | 18.87 ± 0.38 | 18.06 ± 0.84 | 20.06 ± 1.58 | 17.84 ± 0.28 | 18.02 ± 0.93 |
| | % of variation | | 98 | 94 | 104 | | 101 |
| 5. | Residual combined fraction | 24.07 ± 1.93 | 22.89 ± 0.55 | 24.52 ± 1.61 | 22.94 ± 1.17 | 23.79 ± 2.03 | 23.34 ± 0.60 |

| NN 1 | Group II || Group III |||
|---|---|---|---|---|---|---|
| | 2 hours 9 | 4 hours 10 | background 11 | 1 hour 12 | 2 hours 13 | 4 hours 14 |
| 1. | 23.15 ± 1.45 | 22.89 ± 0.70 | 24.60 ± 0.59 | 24.05 ± 0.62 | 24.26 ± 0.34 | 22.94 ± 0.90 |
| | 104 | 103 | | 100 | 101 | 95 |
| 2. | 18.87 ± 2.11 | 19.47 ± 0.28 | 17.05 ± 0.52 | 16.50 ± 0.56 | 17.43 ± 0.49 | 18.77 ± 0.66 |
| | 95 | 98 | | 97 | 102 | 110 |
| 3. | 15.83 ± 0.58 | 16.95 ± 0.84 | 15.95 ± 0.53 | 16.63 ± 0.41 | 17.00 ± 0.50 | 17.01 ± 0.52 |
| | 98 | 105 | | 104 | 107 | 107 |
| 4. | 17.66 ± 0.89 | 19.22 ± 0.45 | 18.37 ± 0.73 | 17.85 ± 0.44 | 19.07 ± 0.42 | 19.89 ± 0.49 |
| | 99 | 108 | | 97 | 104 | 108 |
| 5. | 24.46 ± 1.45 | 21.47 ± 1.33 | 24.03 ± 0.79 | 24.97 ± 1.08 | 22.24 ± 1.20 | 21.39 ± 0.51 |

[1] $p < 0.01$
Group I - healthy europeoids;
Group II - healthy mongoloids;
Group III - alcoholism-suffering patients.

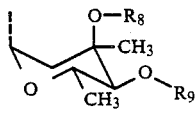

wherein R$_8$ and R$_9$ are as defined in claim 1.

9. A compound of claim 8 wherein R$_9$ is (C$_2$–C$_7$) alkanoyl; or (C$_2$–C$_7$) alkanoyl substituted by chloro, lower alkoxy, phenyl, biphenyl, phenoxy or biphenoxy; or benzoyl or phenylbenzoyl; or benzoyl or phenylbenzoyl or phenoxy or biphenoxy substituted by one or more of halogen, nitro, lower alkoxy, or lower alkyl.

10. A compound of claim 8 wherein R$_8$ is H and R$_9$ is (C$_2$–C$_7$) alkanoyl; or (C$_2$–C$_7$) alkanoyl substituted by chloro, lower alkoxy, phenyl, biphenyl, phenoxy or biphenoxy; or benzoyl or phenylbenzoyl; or benzoyl or phenylbenzoyl or phenoxy or biphenoxy substituted by one or more of halogen, nitro, lower alkoxy, or lower alkyl.

11. A compound of claim 1 wherein R$_1$, R$_2$ and R$_3$ are independently acyl groups; Z is oxygen and R$_4$ is

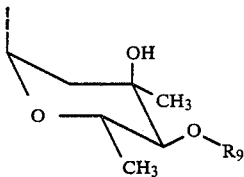

wherein R$_9$ is (C$_2$–C$_6$) alkanoyl.

12. A pharmaceutical composition useful for treating a mammal having a susceptible bacterial infection comprising an antibacterially effective amount of a compound of claim 1 in admixture with a pharmaceutically acceptable carrier therefor.

13. The pharmaceutical composition of claim 12 wherein the compound is a compound of formula I wherein R$_1$, R$_2$ and R$_3$ are independently acyl groups; Z is oxygen and R$_4$ is

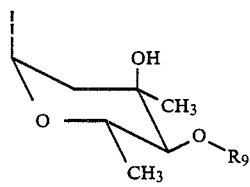

wherein R$_9$ is (C$_2$–C$_6$) alkanoyl.

14. The pharmaceutical composition of claim 12 wherein the compound is a compound of formula I wherein R$_4$ is

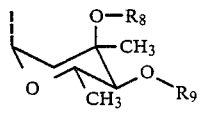

and R$_8$ and R$_9$ are as defined in claim 1.

15. A method of treating susceptible bacterial infections in a small mammal in need of such treatment which comprises administering to the mammal an antibacterially effective amount of a compound of claim 1 or a pharmaceutical composition thereof.

* * * * *